United States Patent
Popp

(10) Patent No.: US 10,060,860 B2
(45) Date of Patent: Aug. 28, 2018

(54) PHARMACEUTICAL DOSAGE FORMS FABRICATED WITH NANOMATERIALS

(71) Applicant: Shane M. Popp, Los Angeles, CA (US)

(72) Inventor: Shane M. Popp, Los Angeles, CA (US)

(73) Assignee: SMP Logic Systems, Los Angeles, CA (US)

( * ) Notice: Subject to any disclaimer, the term of this patent is extended or adjusted under 35 U.S.C. 154(b) by 0 days.

(21) Appl. No.: 14/998,716

(22) Filed: Feb. 5, 2016

(65) Prior Publication Data

US 2016/0245759 A1   Aug. 25, 2016

Related U.S. Application Data

(63) Continuation of application No. 12/215,720, filed on Jun. 25, 2008, now abandoned.

(60) Provisional application No. 60/937,924, filed on Jun. 30, 2007.

(51) Int. Cl.
| | |
|---|---|
| *G01N 21/95* | (2006.01) |
| *A61K 9/107* | (2006.01) |
| *G01N 21/80* | (2006.01) |
| *A61K 39/00* | (2006.01) |
| *A61K 9/51* | (2006.01) |
| *B82Y 15/00* | (2011.01) |

(52) U.S. Cl.
CPC ....... *G01N 21/9508* (2013.01); *A61K 9/1075* (2013.01); *A61K 9/5107* (2013.01); *A61K 9/5192* (2013.01); *A61K 39/00* (2013.01); *B82Y 15/00* (2013.01); *G01N 21/80* (2013.01)

(58) Field of Classification Search
CPC .. G01N 21/9508; G01N 21/80; A61K 9/1075; A61K 9/5107; A61K 9/5192; A61K 39/00; B82Y 15/00
See application file for complete search history.

(56) References Cited

U.S. PATENT DOCUMENTS

| | | |
|---|---|---|
| 1,303,934 A | 5/1919 | Mace |
| 2,052,376 A | 8/1936 | Zellers |
| 2,339,114 A | 1/1944 | Scherer |
| 2,362,181 A | 11/1944 | Zimmerman |
| 2,449,139 A | 9/1948 | Posner |
| 2,623,494 A | 12/1952 | Scherer |
| 2,688,775 A | 9/1954 | Scherer et al. |
| 2,703,047 A | 3/1955 | Scherer et al. |
| 2,845,728 A | 8/1958 | Huber |
| 3,124,840 A | 3/1964 | Taylor et al. |
| 3,203,347 A | 8/1965 | Hansen et al. |
| 3,333,031 A | 7/1967 | Vincent et al. |
| 3,854,581 A | 12/1974 | Jones, Jr. |
| 3,877,360 A | 4/1975 | Vigerstrom |
| 4,109,566 A | 8/1978 | Vigerstrom |
| 4,165,002 A | 8/1979 | Meagher |
| 4,215,104 A | 7/1980 | Ullman et al. |
| 4,263,504 A | 4/1981 | Thomas |
| 4,478,658 A | 10/1984 | Wittwer |
| 4,548,825 A | 10/1985 | Voss et al. |
| 4,629,595 A | 12/1986 | Ito |
| 4,719,112 A | 1/1988 | Mayer et al. |
| 4,735,805 A | 4/1988 | Ni et al. |
| 4,752,364 A | 6/1988 | Dhooge |
| 4,775,439 A | 10/1988 | Seeger et al. |
| 4,820,524 A | 4/1989 | Berta |
| 4,810,867 A | 5/1989 | Speicher |
| 4,874,485 A | 10/1989 | Steele |
| 5,006,362 A | 4/1991 | Hilborn |
| 5,023,437 A | 6/1991 | Speicher |
| 5,031,937 A | 7/1991 | Nellhaus |
| 5,182,659 A | 1/1993 | Clay et al. |
| 5,221,415 A | 6/1993 | Albrecht et al. |
| 5,270,842 A | 12/1993 | Clay et al. |
| 5,298,731 A | 3/1994 | Ett |
| 5,345,815 A | 9/1994 | Albrecht et al. |
| 5,376,771 A | 12/1994 | Roy |
| 5,399,232 A | 3/1995 | Albrecht et al. |
| 5,421,926 A | 6/1995 | Yukinobu et al. |
| 5,422,160 A | 6/1995 | Ratko et al. |
| 5,425,580 A | 6/1995 | Beller |
| 5,483,822 A | 1/1996 | Albrecht et al. |
| 5,512,131 A | 4/1996 | Kumar et al. |
| 5,524,758 A | 6/1996 | Lupul |
| 5,554,822 A | 9/1996 | Gilpin et al. |
| 5,580,827 A | 12/1996 | Akamine |
| 5,595,942 A | 1/1997 | Albrecht et al. |
| 5,603,894 A | 2/1997 | Aikus et al. |
| 5,662,962 A | 9/1997 | Kawata et al. |
| 5,690,978 A | 11/1997 | Yin et al. |
| 5,700,998 A | 12/1997 | Palti |
| 5,712,731 A | 1/1998 | Drinkwater et al. |
| 5,729,365 A | 3/1998 | Sweatt |
| 5,742,377 A | 4/1998 | Minne et al. |
| 5,762,263 A | 6/1998 | Chamberlain, IV |
| 5,772,905 A | 6/1998 | Chou |
| 5,811,775 A | 9/1998 | Lee |
| 5,845,264 A | 12/1998 | Nellhaus |

(Continued)

FOREIGN PATENT DOCUMENTS

| | | |
|---|---|---|
| EP | 0 112 183 A2 | 6/1984 |
| EP | 0 174 868 B1 | 6/1991 |

(Continued)

OTHER PUBLICATIONS

Hard Gelatin Capsules Today and Tomorrow, Stegemann, et. al., Capsugel Library, 2nd Ed. 2002, pp. 1-23.

(Continued)

*Primary Examiner* — Johann R Richter
*Assistant Examiner* — Genevieve S Alley

(57) ABSTRACT

Nanomaterials fabricated to pharmaceutical dosage forms are disclosed. The nanomaterials are useful to provide a plurality of analysis to the dosage form. Consequently, the nanomaterials provide a means to perform quality testing on a continuous basis throughout the supply chain, including the cold chain whereby manufacturers and distributors can achieve greater product integrity and longer shelf life and ultimately minimize cost. The end user benefits in obtaining the highest quality drugs at the time of need.

5 Claims, 6 Drawing Sheets

(56) References Cited

U.S. PATENT DOCUMENTS

| | | | |
|---|---|---|---|
| 5,874,214 A * | 2/1999 | Nova | B01J 19/0046 365/151 |
| 5,885,609 A | 3/1999 | Amiji | |
| 5,904,927 A | 5/1999 | Amiji | |
| 5,907,144 A | 5/1999 | Poon et al. | |
| 5,952,542 A | 9/1999 | Steele | |
| 5,992,742 A | 11/1999 | Sullivan et al. | |
| 6,006,415 A | 12/1999 | Schaefer et al. | |
| 6,024,981 A | 2/2000 | Khankari et al. | |
| 6,075,585 A | 6/2000 | Minne et al. | |
| 6,085,903 A | 7/2000 | Jotcham et al. | |
| 6,138,555 A | 10/2000 | Hata | |
| 6,183,878 B1 | 2/2001 | Berneth et al. | |
| 6,193,999 B1 | 2/2001 | Gennadios | |
| 6,214,376 B1 | 4/2001 | Gennadios | |
| 6,220,333 B1 | 4/2001 | Cantwell | |
| 6,251,426 B1 | 6/2001 | Gullapalli | |
| 6,258,380 B1 | 7/2001 | Overholt | |
| 6,309,668 B1 | 10/2001 | Bastin et al. | |
| 6,312,911 B1 | 11/2001 | Bancroft et al. | |
| 6,316,027 B1 | 11/2001 | Johnson et al. | |
| 6,316,029 B1 | 11/2001 | Jain et al. | |
| 6,375,870 B1 | 4/2002 | Visovsky et al. | |
| 6,391,237 B1 | 5/2002 | Kearney et al. | |
| 6,402,932 B1 | 6/2002 | Bremer et al. | |
| 6,482,516 B1 | 11/2002 | Sadek et al. | |
| 6,543,692 B1 | 4/2003 | Nellhaus et al. | |
| 6,558,957 B1 | 5/2003 | Roinestad et al. | |
| 6,573,369 B2 | 6/2003 | Henderson et al. | |
| 6,635,311 B1 | 10/2003 | Mirkin et al. | |
| 6,641,036 B1 | 11/2003 | Kalinowski | |
| 6,642,129 B2 | 11/2003 | Liu et al. | |
| 6,651,338 B2 | 11/2003 | Helm | |
| 6,694,873 B1 | 2/2004 | LaBelle et al. | |
| 6,709,669 B1 | 3/2004 | Murray et al. | |
| 6,726,928 B2 | 4/2004 | Yarwood et al. | |
| 6,773,716 B2 | 8/2004 | Ream et al. | |
| 6,799,725 B1 | 10/2004 | Hess et al. | |
| 6,827,979 B2 | 12/2004 | Mirkin et al. | |
| 6,830,153 B2 | 12/2004 | French et al. | |
| 6,860,405 B1 | 3/2005 | Poynter | |
| 6,867,443 B2 | 3/2005 | Liu et al. | |
| 6,884,060 B2 | 4/2005 | Tanner et al. | |
| 6,894,660 B2 | 5/2005 | Sanogo | |
| 6,896,890 B2 | 5/2005 | Singh et al. | |
| 6,929,412 B1 | 8/2005 | Barrus et al. | |
| 6,946,951 B2 | 9/2005 | Cole et al. | |
| 6,949,256 B2 | 9/2005 | Fonkwe et al. | |
| 6,984,404 B1 | 1/2006 | Talton et al. | |
| 6,998,115 B2 | 2/2006 | Langer et al. | |
| 6,998,228 B2 | 2/2006 | Henderson et al. | |
| 7,005,378 B2 | 2/2006 | Crocker et al. | |
| 7,006,294 B2 | 2/2006 | Steenblik et al. | |
| 7,021,163 B2 | 4/2006 | Kyne | |
| 7,034,854 B2 | 4/2006 | Cruchon-Dupeyrat et al. | |
| 7,060,977 B1 | 6/2006 | Dupeyrat et al. | |
| 7,083,805 B2 | 8/2006 | Begleiter | |
| 7,098,056 B2 | 8/2006 | Demers | |
| 7,102,656 B2 | 9/2006 | Mirkin et al. | |
| RE39,347 E | 10/2006 | Ikemoto | |
| 7,115,297 B2 | 10/2006 | Stillman | |
| 7,135,054 B2 | 11/2006 | Jin et al. | |
| 7,138,133 B2 | 11/2006 | Dobrozsi et al. | |
| 7,163,696 B2 | 1/2007 | Davis et al. | |
| 7,195,780 B2 | 3/2007 | Dennis et al. | |
| 7,199,305 B2 | 4/2007 | Cruchon-Dupeyrat et al. | |
| 7,220,434 B2 | 5/2007 | Desai et al. | |
| 7,221,259 B2 | 5/2007 | Cole | |
| 7,223,438 B2 | 5/2007 | Mirkin et al. | |
| 7,225,082 B1 | 5/2007 | Natan et al. | |
| 7,267,275 B2 | 9/2007 | Cox, Jr. et al. | |
| 7,273,636 B2 | 9/2007 | Mirkin et al. | |
| 7,279,046 B2 | 10/2007 | Eby et al. | |
| 7,288,320 B2 | 10/2007 | Steenblik et al. | |
| 7,326,380 B2 | 2/2008 | Mirkin et al. | |
| 7,361,310 B1 | 4/2008 | Mirkin et al. | |
| 7,516,128 B2 | 4/2009 | Colby et al. | |
| 7,531,080 B2 | 5/2009 | Carson et al. | |
| 7,569,340 B2 | 8/2009 | Mirkin et al. | |
| 7,710,269 B2 | 5/2010 | Reep | |
| 7,722,928 B2 | 5/2010 | Mirkin et al. | |
| D631,537 S | 1/2011 | Sadler et al. | |
| 7,868,768 B2 | 1/2011 | Angell et al. | |
| 7,969,307 B2 | 6/2011 | Peeters | |
| 8,069,782 B2 | 12/2011 | Fragala et al. | |
| 2001/0034673 A1 | 10/2001 | Yang et al. | |
| 2001/0054901 A1 | 12/2001 | Puttkammer | |
| 2002/0054680 A1 | 5/2002 | Huang et al. | |
| 2003/0038033 A1 | 2/2003 | Harker et al. | |
| 2003/0068446 A1 | 4/2003 | Mirkin et al. | |
| 2003/0072716 A1 | 4/2003 | Poovathinthodiyil et al. | |
| 2003/0089899 A1 * | 5/2003 | Lieber | B82Y 10/00 257/9 |
| 2003/0127508 A1 | 7/2003 | Jones | |
| 2003/0133985 A1 | 7/2003 | Louie-Helm et al. | |
| 2003/0162404 A1 | 8/2003 | Chang | |
| 2003/0179364 A1 | 9/2003 | Steenblik et al. | |
| 2003/0185967 A1 | 10/2003 | Eby et al. | |
| 2003/0197366 A1 | 10/2003 | Kusterbeck | |
| 2004/0006486 A1 | 1/2004 | Schmidt et al. | |
| 2004/0008330 A1 | 1/2004 | Mirkin et al. | |
| 2004/0023948 A1 | 2/2004 | Green et al. | |
| 2004/0026681 A1 | 2/2004 | Cruchon-Dupeyrat et al. | |
| 2004/0028694 A1 | 2/2004 | Young et al. | |
| 2004/0075121 A1 | 4/2004 | Yu et al. | |
| 2004/0099740 A1 | 5/2004 | Chresand et al. | |
| 2004/0131843 A1 | 7/2004 | Mirkin et al. | |
| 2004/0142106 A1 | 7/2004 | Mirkin et al. | |
| 2004/0166520 A1 | 8/2004 | Connolly | |
| 2004/0172341 A1 | 9/2004 | Aoyama et al. | |
| 2004/0175631 A1 | 9/2004 | Crocker et al. | |
| 2004/0245343 A1 | 12/2004 | Depta | |
| 2005/0009206 A1 | 1/2005 | Mirkin et al. | |
| 2005/0019434 A1 | 1/2005 | Duvert et al. | |
| 2005/0038039 A1 | 2/2005 | Fanara et al. | |
| 2005/0110614 A1 | 5/2005 | Coates et al. | |
| 2005/0143321 A1 | 6/2005 | Vardosanidze et al. | |
| 2005/0172704 A1 | 8/2005 | Mirkin et al. | |
| 2005/0214356 A1 | 9/2005 | Joyce | |
| 2005/0235869 A1 | 10/2005 | Cruchon-Dupeyrat et al. | |
| 2005/0255237 A1 | 11/2005 | Zhang et al. | |
| 2005/0272885 A1 | 12/2005 | Mirkin et al. | |
| 2005/0277710 A1 | 12/2005 | Joyce et al. | |
| 2006/0011549 A1 | 1/2006 | Wormsbecher | |
| 2006/0015536 A1 | 1/2006 | Buchanan et al. | |
| 2006/0040057 A1 | 2/2006 | Sheehan et al. | |
| 2006/0078623 A1 | 4/2006 | Dhoot et al. | |
| 2006/0087051 A1 | 4/2006 | Bunick et al. | |
| 2006/0099246 A1 | 5/2006 | Tanner et al. | |
| 2006/0100278 A1 | 5/2006 | Cooper et al. | |
| 2006/0106718 A1 | 5/2006 | Spellman et al. | |
| 2006/0115495 A1 | 6/2006 | Yacaman et al. | |
| 2006/0153916 A1 | 7/2006 | Vaya et al. | |
| 2006/0196945 A1 | 9/2006 | Mendels | |
| 2006/0226234 A1 | 10/2006 | Kettinger et al. | |
| 2006/0232375 A1 | 10/2006 | Loussert et al. | |
| 2006/0242740 A1 | 10/2006 | Collier et al. | |
| 2006/0286082 A1 | 12/2006 | Kurzweil | |
| 2006/0289640 A1 | 12/2006 | Mercure et al. | |
| 2007/0020197 A1 | 1/2007 | Galli et al. | |
| 2007/0026064 A1 | 2/2007 | Yoder et al. | |
| 2007/0086625 A1 | 4/2007 | Polli et al. | |
| 2007/0087172 A1 | 4/2007 | Mirkin et al. | |
| 2007/0115865 A1 | 5/2007 | Jokela et al. | |
| 2007/0141118 A1 | 6/2007 | Damico et al. | |
| 2007/0154714 A1 | 7/2007 | Mirkin et al. | |
| 2007/0264481 A1 | 11/2007 | DeSimone et al. | |
| 2007/0275230 A1 | 11/2007 | Murphy et al. | |
| 2007/0294101 A1 | 12/2007 | Dalal et al. | |
| 2007/0298253 A1 | 12/2007 | Hata et al. | |
| 2008/0038355 A1 | 2/2008 | Yang et al. | |
| 2008/0042837 A1 | 2/2008 | Burke | |
| 2008/0055344 A1 | 3/2008 | Haaheim et al. | |
| 2008/0055598 A1 | 3/2008 | Haaheim | |

(56) References Cited

U.S. PATENT DOCUMENTS

| | | | |
|---|---|---|---|
| 2008/0145429 A1 | 6/2008 | Leyendecker et al. |
| 2008/0166411 A1 | 7/2008 | Shah et al. |
| 2008/0284569 A1 | 11/2008 | Shah |
| 2008/0284597 A1 | 11/2008 | Shah |
| 2008/0284598 A1 | 11/2008 | Shah |
| 2009/0004231 A1 | 1/2009 | Popp |
| 2009/0009332 A1 | 1/2009 | Nunez et al. |
| 2009/0023804 A1 | 1/2009 | Baugh et al. |
| 2009/0027208 A1 | 1/2009 | Martin et al. |
| 2009/0076115 A1 | 3/2009 | Wharton et al. |
| 2009/0143246 A1 | 6/2009 | Mirkin et al. |
| 2009/0169586 A1 | 7/2009 | Tracton |
| 2009/0169619 A1 | 7/2009 | Gande et al. |
| 2009/0220789 A1 | 9/2009 | DeSimone et al. |
| 2009/0223990 A1 | 9/2009 | Bailey et al. |
| 2010/0048427 A1 | 2/2010 | Mirkin et al. |
| 2010/0062194 A1 | 3/2010 | Sun |
| 2010/0066502 A1 | 3/2010 | Giraud et al. |
| 2010/0111294 A1 | 5/2010 | Soppera et al. |
| 2010/0297027 A1 | 11/2010 | Loiret-Bernal et al. |
| 2011/0053593 A1 | 3/2011 | Tanabe et al. |
| 2011/0091068 A1 | 4/2011 | Stuck et al. |
| 2011/0165569 A1 | 7/2011 | Macula |
| 2011/0167010 A1 | 7/2011 | Soppera et al. |
| 2011/0186629 A1 | 8/2011 | Stuck et al. |
| 2011/0188051 A1 | 8/2011 | Stuck et al. |
| 2012/0158610 A1 | 6/2012 | Botvinick et al. |
| 2012/0175412 A1 | 7/2012 | Grabiner et al. |
| 2012/0239938 A1 | 9/2012 | Thurber et al. |
| 2013/0006877 A1 | 1/2013 | Brooks et al. |
| 2013/0080183 A1 | 3/2013 | Bond |
| 2013/0173483 A1 | 7/2013 | Brooks et al. |

FOREIGN PATENT DOCUMENTS

| | | | |
|---|---|---|---|
| EP | 0721325 B1 | | 11/2000 |
| EP | 0822810 B1 | | 7/2002 |
| EP | 1009358 B1 | | 10/2002 |
| EP | 0835103 B1 | | 6/2005 |
| EP | 1131054 B1 | | 2/2006 |
| WO | WO87/00817 | | 2/1987 |
| WO | WO 91/03747 | | 3/1991 |
| WO | WO93/04674 | | 3/1993 |
| WO | WO95/09608 | | 4/1995 |
| WO | WO96/33702 | | 10/1996 |
| WO | WO96/35414 | | 11/1996 |
| WO | WO98/42294 | | 10/1998 |
| WO | WO 01/37266 A1 | | 5/2001 |
| WO | WO03/049275 A1 | | 6/2003 |
| WO | WO2004/001019 A2 | | 12/2003 |
| WO | WO2004/096085 A2 | | 11/2004 |
| WO | WO 2005/001889 | * | 1/2005 |

OTHER PUBLICATIONS

Cold Chains are Hot! —Mastering the Challenges of Temperature-Sensitive Distribution in Supply Chains, Reed, Chainlink Res. Feb. 2005, pp. 1-44.
Do it by Design: An Introduction into Human Factors in MEdical Devices, Sawyer, U.S. Dept. of Health and Humans Srvs., Dec. 1996, pp. 1-55.
Guidance for Industry, Dosage and Administration Section of Labeling for Human Prescription . . . , U.S. Dept. of Health and Human Services, Apr. 2007, pp. 1-13.
Guidance for Industry, Dissolution Testing of Immediate Release Solid Oral Dosage Forms, U.S. Dept. of Health and Human Srvs., Aug. 1997, pp. 1-17.
Guidance for Industry, Container Closure Systems for Packaging Human Drugs and Biologics, U.S. Dept. of Health and Human Srvs., May 1999, pp. 1-56.
Drug safety: Improvement Needed in FDA's Postmarket Decision-Making and Oversight Process, Gov. Accountability Office, Mar. 2006, pp. 1-67.
Phase Transformations in Solid Pharmaceutical Materials Studied by AFM, ESCA, DSC, and SAXS, Mahlin, Uppsala Univ. 2004, pp. 1-72.
Studies on Aqueous Film Coating of Tablets Performed in a Side-Vented Pan Coater, Ruotalainen, Univ. of Helsinki, 2003, pp. 1-53.
Preparation and Characterization of Poly(Lactic Acid) Nanoparticles for Pharmaceutical Use, Hirsjrvi, Univ. of Helsinki, Feb. 1, 2008, pp. 1-50.
Nanotechnology Approaches to Solving the Problems of Poorly Water-Soluble Drugs, Rogheih, et. al., Drug Discovery World, Summer 2005, pp. 1-6.
Nanomedicine—Highlights of the Latest Biomedical Developments Diagnostics and Drugs and Thier Risk Management, Luotola, Orion Group, Sep. 14, 2006, pp. 1-23.
Particle Size and Shape Characterization of Nano and Submicron Liquid Dispersions, Tinke, et. al., American Pharma. Rev. Sep. 2006, pp. 1-5.
Potency Testing of Bacterial Vaccines for Human Use, Habig, Veterinary Microbiology, 37(1993)343-351.
Nanoparticles for Multifunctional Drug Delivery Systems, Qin, Royal Institute of Technology, 2007, pp. 1-78.
Application of Micro- and Nano-Electromechanical Devices to Drug Discovery, Staples, et. al., Pharm. Res., vol. 23, No. 5 (May 2006) pp. 847-863.
PEGylated Nanoparticles for Biological and Pharmaceutical Applications, Otsuka, et. al., Adv. Drug Delivery Rev., 55(2003)403-419.
Nanotechnology on Duty in Medical Applications, Kubik, et. al., Current Pharm. Biotechnology, 2005, 6, pp. 17-33.
Näñotechnology and Pharmaceutical Inhalation Aerosols, Patel, Indian J. Exp. Bio., vol. 45, pp. 166-174 (Feb. 2007).
Terahertz Pulsed Imaging Identifies Counterfeit Products, Pederson, Article, The International Society for Optical Engineering, pp. 1-3 (Jun. 17, 2007).
Nanotechnology Protects Capsules from Counterfeiting and Diversion, Press Release: Posted by Healthcare Packaging, pp. 1-3 (Oct. 15, 2010).
Elemental Imaging for Pharmaceutical Tablet Formulation Analysis by Micro X-Ray Flourescence, Miller, et. al., Adv. in X-ray Analysis, vol. 48, pp. 274-283 (2005).
Recent Applications of Chemical Imaging to Pharmaceutical Process Monitoring and Quality Control, Gowen, et. al., J. Pharma. and Biopharma., vol. 69(1), pp. 10-22 (May 1, 2008).
Pharmaceutical Counterfeiting, Deisingh, Analyst (2005) 130. pp. 271-279 (Dec. 14, 2004).
IBM Solution for Pharmaceutical Track and Trace, IBM Corporation, pp. 1-7 (Aug. 2007).
WSN Based Intelligent Cold Chain Management, Fu, et. al., 6th International Conference on Manufacturing Research, pp. 353-360 (Sep. 9, 2008).
Encoding and Reading of Codes on Glass Containers for Pharmaceutical Products, Voldrich, et. al., Pharm. Ind. 71, No. 10, 1770-1774 (2009).

* cited by examiner

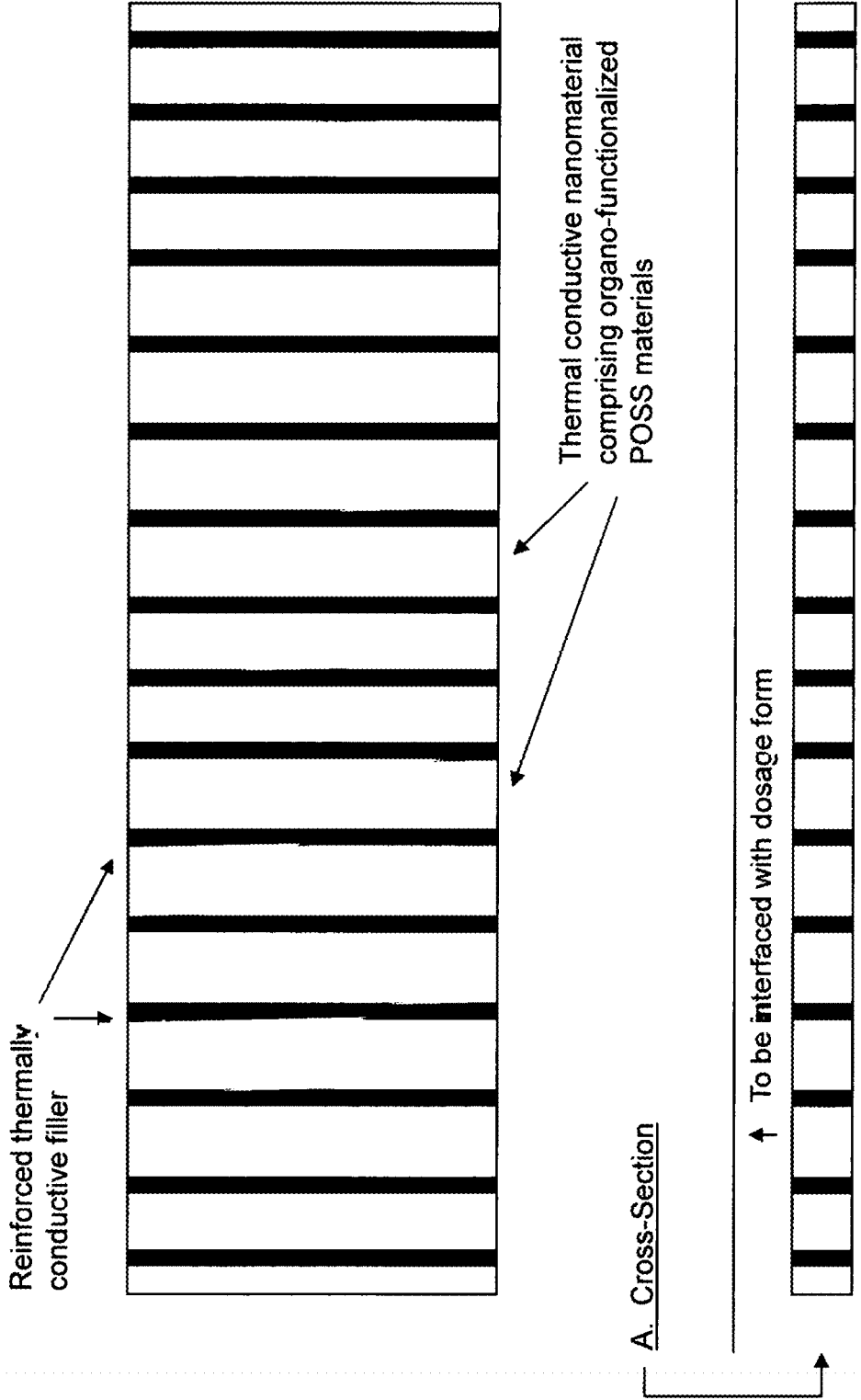

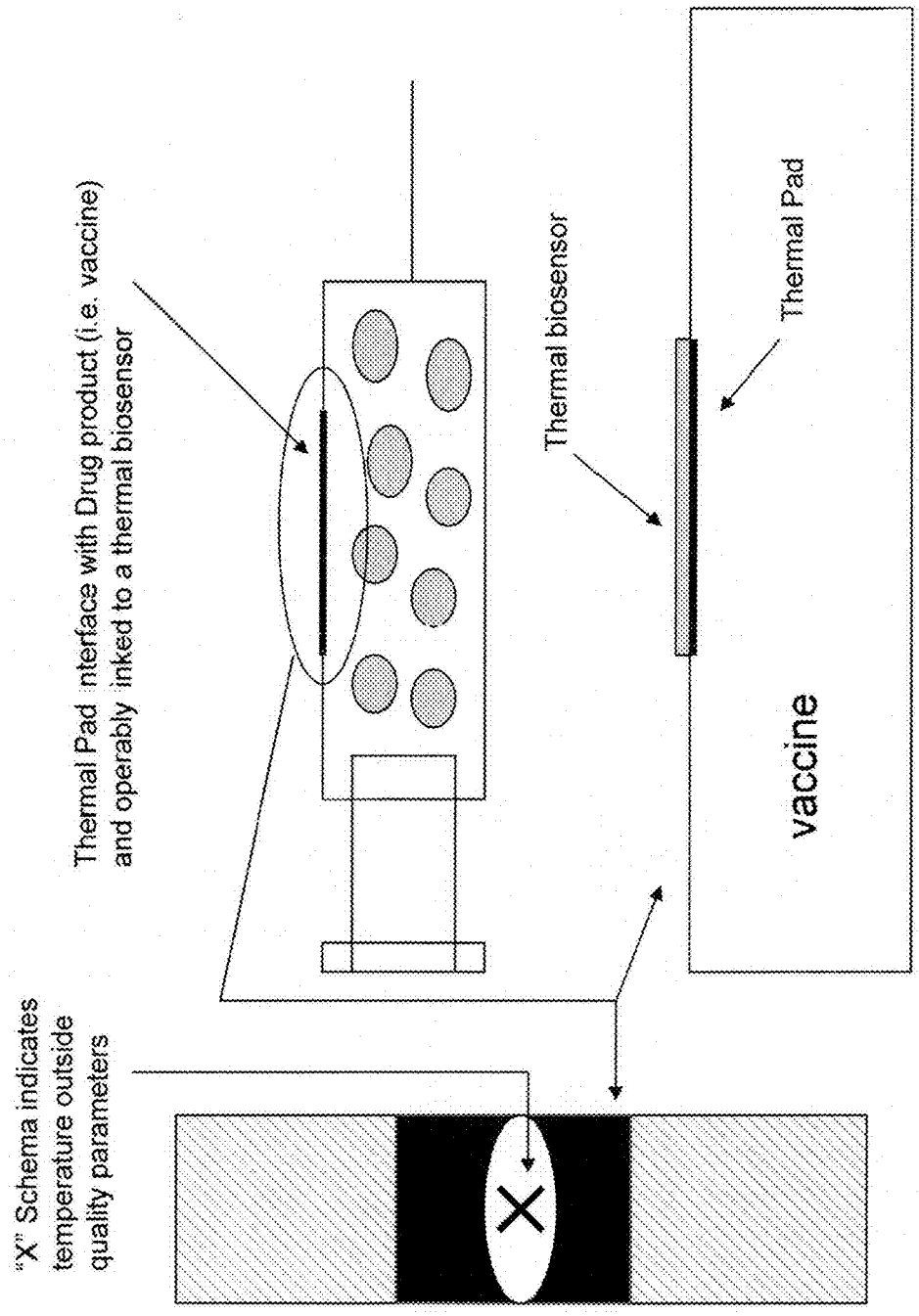
Figure 2: Thermal Interface Pad Fabricated into a Pre-Fill Syringe to Monitor Temperature of Vaccine

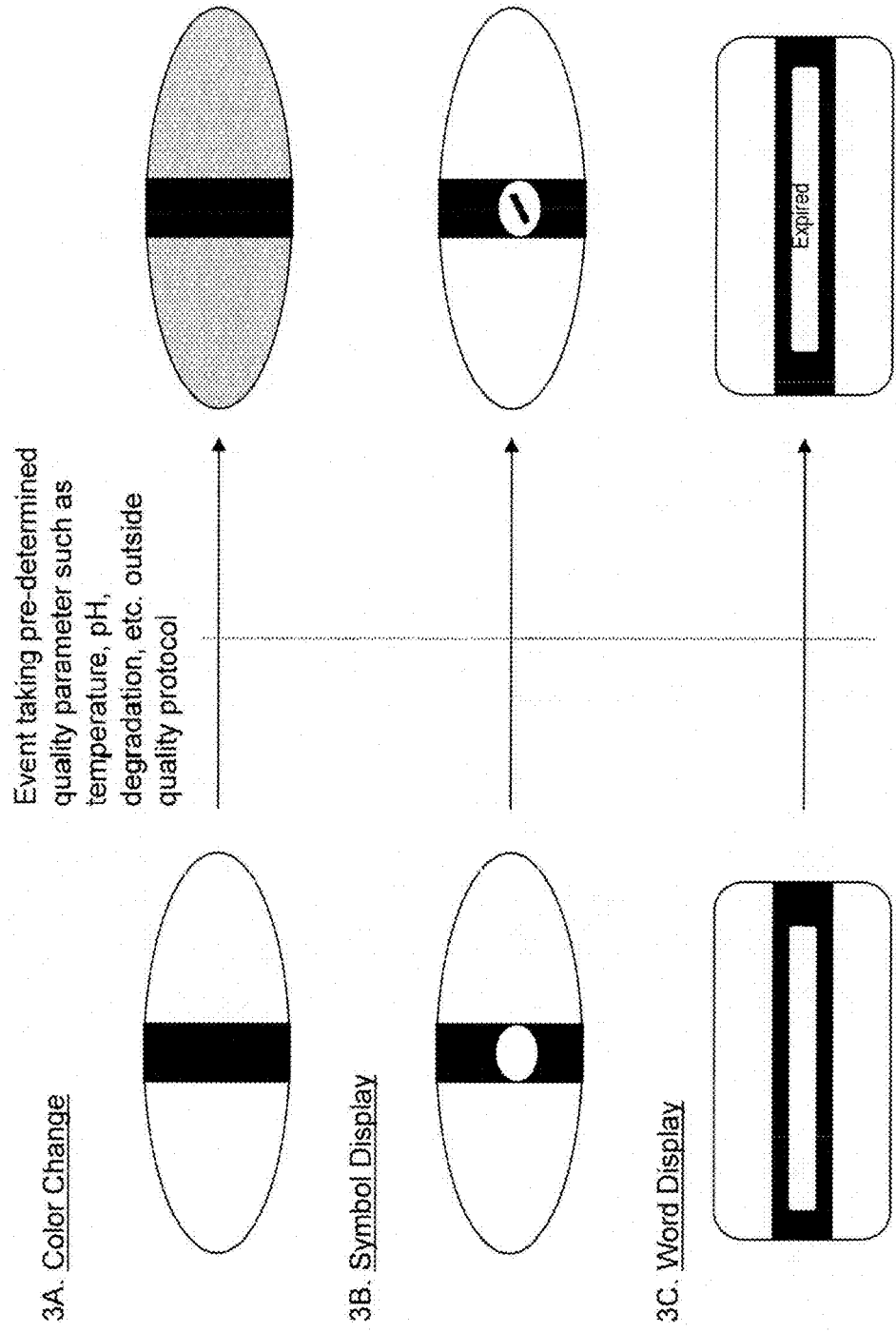

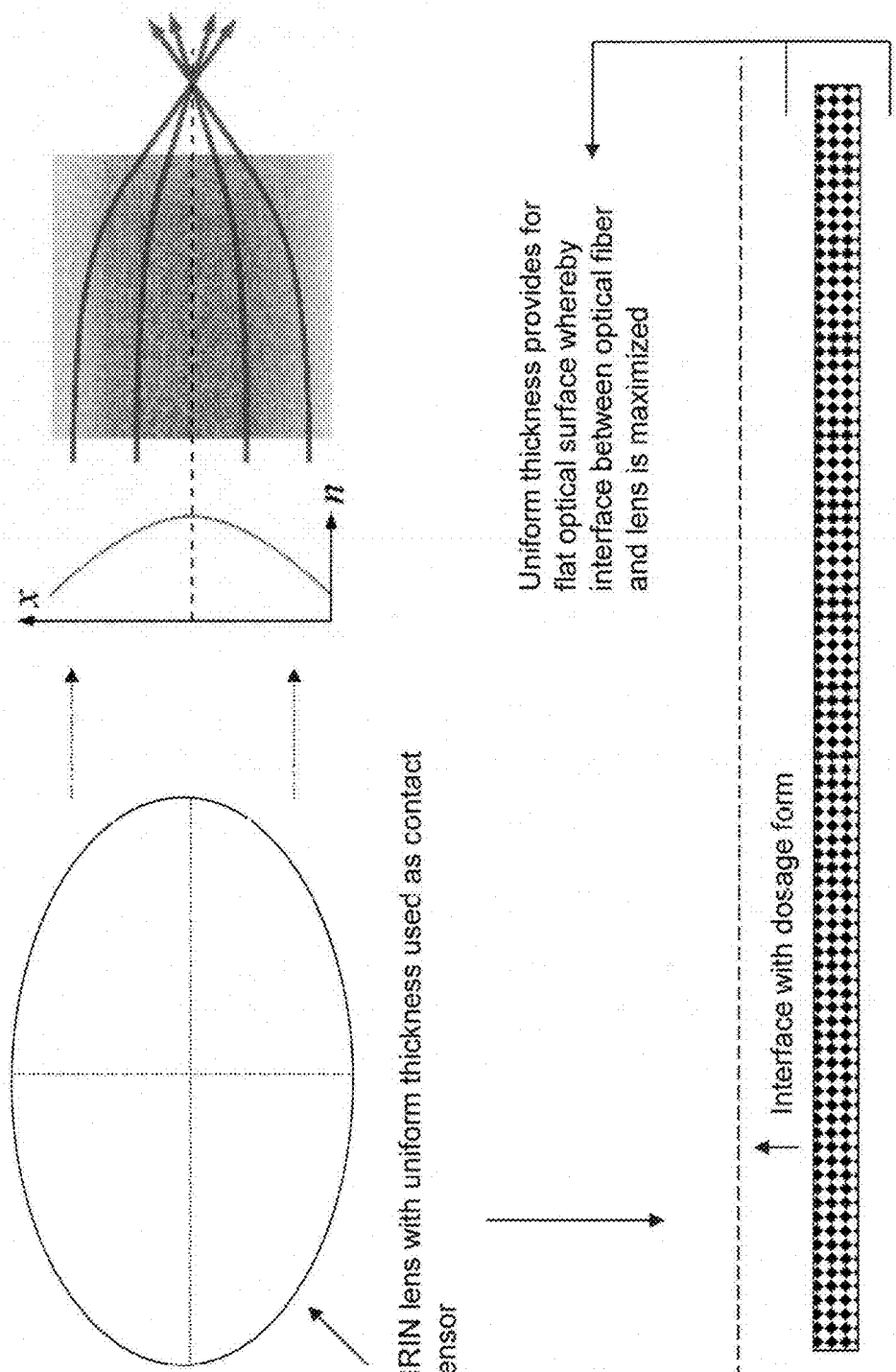

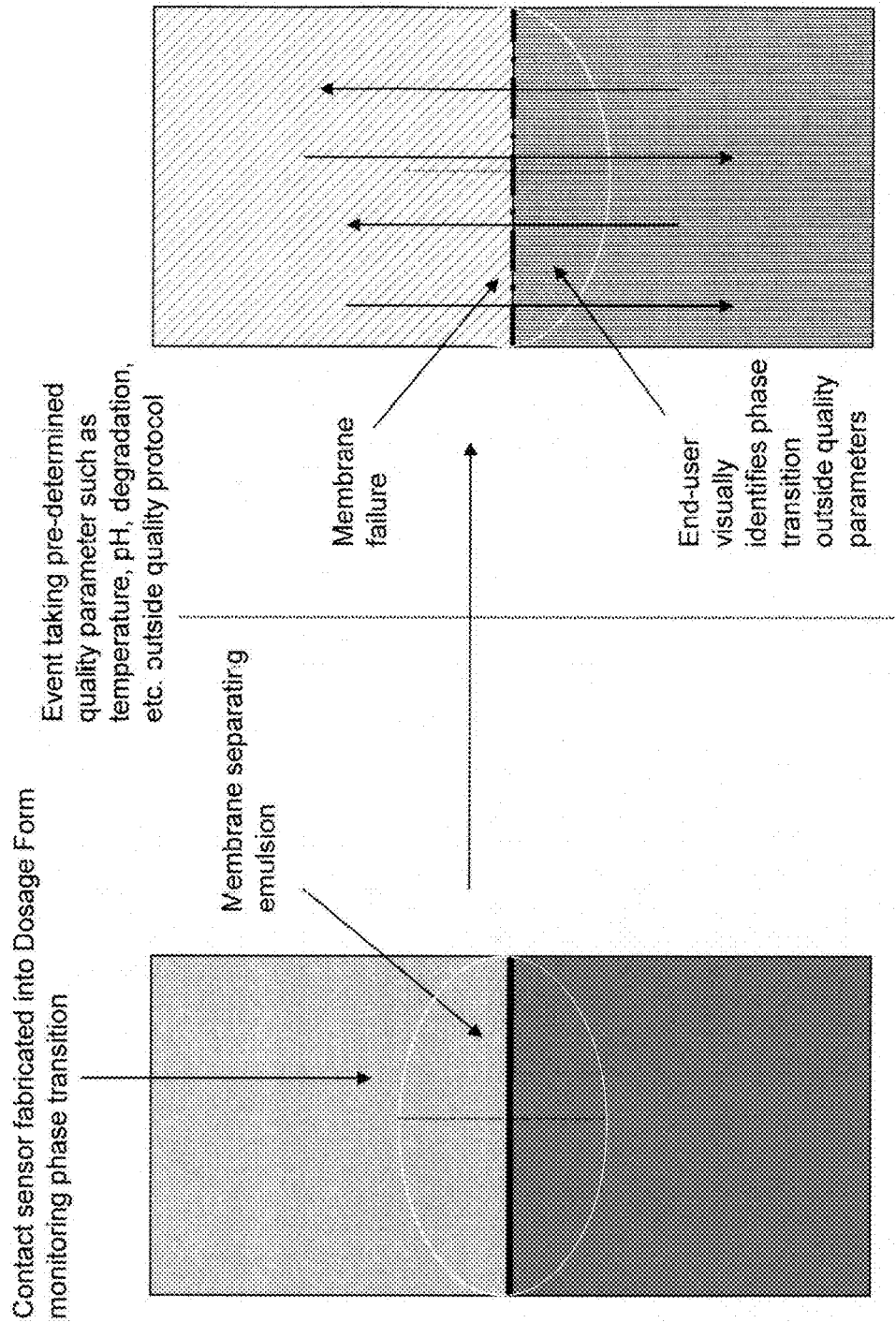
Figure 5: Optical Contact Sensor Fabricated into Dosage Form to Monitor Phase Transition of Emulsion

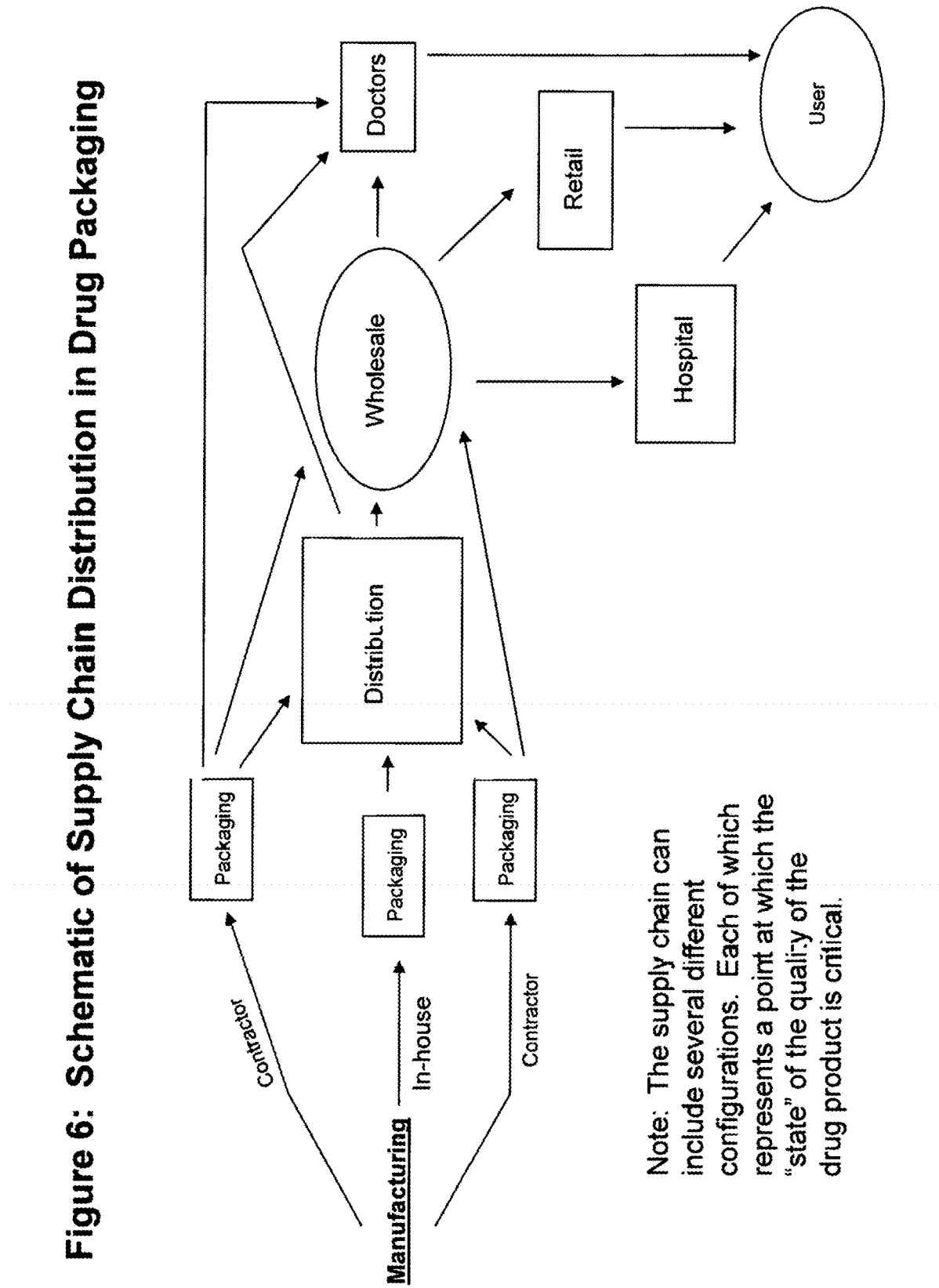
Figure 6: Schematic of Supply Chain Distribution in Drug Packaging

PHARMACEUTICAL DOSAGE FORMS FABRICATED WITH NANOMATERIALS

CROSS-REFERENCE TO RELATED APPLICATIONS

This application is a continuation of U.S. patent application Ser. No. 12/215,720 filed 25 Jun. 2008, which claims priority to U.S. Provisional Patent Application No. 60/937,924 filed 30 Jun. 2007, the contents of which are fully incorporated by reference herein.

STATEMENT OF RIGHTS TO INVENTIONS MADE UNDER FEDERALLY SPONSORED RESEARCH

Not applicable.

FIELD OF THE INVENTION

The invention described herein relates to the field of pharmaceutical dosage forms and nanotechnologies. Specifically, nanomaterials used for the monitoring of quality in pharmaceutical dosage form technologies. The invention further relates to the enhancement of nanotechnologies to produce higher quality more efficient drug storage forms whereby the shelf life of high quality drugs will increase.

BACKGROUND OF THE INVENTION

We endeavor to further the state of the art using nanomaterials in the field of pharmaceutical dosage forms and formulation technology.

Nanotechnology is a field of applied science and technology covering a broad range of topics. The main unifying theme is the control of matter on a scale smaller than one micrometer as well as the fabrication of devices on this same length scale. Worldwide research is currently being conducted in countless areas to discover new and useful areas where nanotechnology can be exploited commercially. The research involves potential utility in industrial applications, such as pharmaceutical packaging as well as other areas of medicine and bio-energy just to name a few.

Despite the apparent simplicity of this definition, nanotechnology actually encompasses diverse lines of inquiry. Nanotechnology cuts across many disciplines, including colloidal science, chemistry, applied physics, biology. It could variously be seen as an extension of existing sciences into the nanoscale, or as a recasting of existing sciences using a newer, more modern term.

Two main approaches are used in nanotechnology. One is a "bottom-up" approach where materials and devices are built from molecular components which assemble themselves chemically using principles of molecular recognition. The other being a "top-down" approach where nano-objects are constructed from larger entities without atomic-level control.

Nanomaterials are materials having unique properties arising from their nanoscale dimensions. The use of nanoscale materials can also be used for bulk applications. In fact, most present commercial applications of nanotechnology are of this flavor.

Nanomaterials from a "top-down" design have certain scaling deficiencies which must be assessed. For example, A number of physical phenomena become noticeably pronounced as the size of the system decreases. These include statistical mechanical effects, as well as quantum mechanical effects, for example the "quantum size effect" where the electronic properties of solids are altered with great reductions in particle size. This effect does not come into play by going from macro to micro dimensions. However, it becomes dominant when the nanometer size range is reached. Additionally, a number of physical properties change when compared to macroscopic systems. One example is the increase in surface area to volume of materials. This catalytic activity also opens potential risks in their interaction with biomaterials.

Additionally, materials reduced to the nanoscale can suddenly show very different properties compared to what they exhibit on a macroscale, enabling unique applications. For instance, opaque substances become transparent (copper); inert materials become catalysts (platinum); stable materials turn combustible (aluminum); solids turn into liquids at room temperature (gold); insulators become conductors (silicon) to name a few.

Additionally, nanosize powder particles are important for the achievement of uniform nanoporosity and similar applications. However, the tendency of small particles to form clumps ("agglomerates") is a serious technological problem that impedes such applications.

Another deficiency is that the volume of an object decreases as the third power of its linear dimensions, but the surface area only decreases as its second power. This somewhat subtle and unavoidable principle has huge ramifications. For example the power of a drill (or any other machine) is proportional to the volume, while the friction of the drill's bearings and gears is proportional to their surface area. For a normal-sized drill, the power of the device is enough to handily overcome any traction. However, scaling its length down by a factor of 1000, for example, decreases its power by $1000^3$ (a factor of a billion) while reducing the friction by only $1000^2$ (a factor of "only" a million). Proportionally it has 1000 times less power per unit friction than the original drill. If the original friction-to-power ratio was, say, 1%, that implies the smaller drill will have 10 times as much friction as power. The drill is useless.

This is why, while super-miniature electronic integrated circuits can be made to function, the same technology cannot be used to make functional mechanical devices in miniature.

Nanomaterials from a "bottom-up" design also have certain deficiencies which must be assessed. Modern synthetic chemistry has reached the point where it is possible to prepare small molecules to almost any structure. These methods are used today to produce a wide variety of useful chemicals such as pharmaceuticals or commercial polymers. However, the ability of this to extend into supramolecular assemblies consisting of many molecules arranged in a well defined manner is problematic. Such bottom-up approaches should, broadly speaking, be able to produce devices in parallel and much cheaper than top-down methods. However, most useful structures require complex and thermodynamically unlikely arrangements of atoms. The basic laws of probability and entropy make it very unlikely that atoms will "self-assemble" in useful configurations, or can be easily and economically nudged to do so. About the only example of this is a crystal growing, for which Nanotechnology cannot take any credit.

Given the deficiencies associated with "top-down" and "bottom-up" nanomaterials, it becomes clear that providing a functional approach to nanotechnology (i.e. the development of nanomaterials of a desired functionality) can be problematic.

Finally, implementing nanotechnologies in highly-regulated bulk packaging applications, such as pharmaceutical formulation and dosage forms, only compounds problems. The present invention overcomes these problems.

In relation to pharmaceutical dosage forms, soft gelatin capsules, now more commonly known as softgels, have been well known and widely used for many years. Softgels generally comprise an outer shell primarily made of gelatin, a plasticizer, and water, and a fill contained within the shell. However, other materials as a substitute for gelatin can be used, such as gum acacia and other non-gelatin substitutes. The fill may be selected from any of a wide variety of substances that are compatible with the shell. Softgels are widely used in the pharmaceutical industry as an oral dosage form containing many different types of pharmaceutical and vitamin products. In addition to use as an oral dosage form for drugs and vitamins, soft gelatin capsules or softgels are also designed for use as suppositories for rectal or vaginal use. Other uses are for topical and ophthalmic preparations and the like. The cosmetic industry also uses softgels as a specialized package for various types of perfumes, oils, shampoos, skin creams and the like. Softgels are available in a great variety of sizes and shapes, including round shapes, oval shapes, oblong shapes, tube shapes and other special types of shapes such as stars. The finished capsules or softgels can be made in a variety of colors. In addition, opacifiers may be added to the shell.

Although softgels can be made in a wide variety of shapes, sizes and colors, because of the wide range of use of softgels, there is a definite need to provide improved means of monitoring quality of the dosage form (i.e. capsule) and other means of identification. In this regard, it is quite common today to have an indicia of some type printed on each softgel after formation. The printing material may be any suitable dye or pigment. In some equipment, this has the disadvantage of requiring the use of an additional machine that will align the softgels and hold them in a desired oriented position for the application of the dye or ink. The use of additional equipment and procedural steps adds to the overall cost of manufacture of the softgels and, therefore, this system is considered disadvantageous. Also, the printing of each softgel can be done over only a limited portion of the exterior surface of the softgel and may not be readily read or even seen by the consumer. Specific examples of known processes and machines used for applying some type of identification on the softgels are those shown, for example, in Power (Posner) U.S. Pat. No. 2,449,139; Scherer U.S. Pat. No. 2,623,494; Scherer U.S. Pat. No. 2,688,775; Scherer U.S. Pat. No. 2,688,775; Taylor U.S. Pat. No. 3,124,840; Hansen U.S. Pat. No. 3,203,347; and Vincent U.S. Pat. No. 3,333,031.

In the rotary die process for manufacturing softgels, two gelatin ribbons are prepared, fed simultaneously to the fill area, and simultaneously and continuously filled, formed, hermetically sealed, and automatically cut between two rotary dies. The Scherer U.S. Pat. No. 2,623,494 relates to a banding machine for softgels. In this machine, the identifying band is applied to each individual capsule after the capsule is formed. The Scherer U.S. Pat. No. 2,688,775 shows a method for applying a brand to the exterior surface of a gelatin capsule. The Scherer U.S. Pat. No. 2,703,047 discloses a similar system of branding the filled capsules. In the Taylor U.S. Pat. No. 3,124,840, a printing element is provided in order to print on the gelatin strip prior to the formation of the capsule. The Hansen U.S. Pat. No. 3,203,347 shows a marking fluid that is printed on the gelatin ribbon used to make the softgels. The Vincent U.S. Pat. No. 3,333,031 shows dying of the gelatin strip before capsule formation. Even though efforts have been made to manufacture gelatin capsule and distinguish them from those of others by using different shapes, sizes, colors, color combinations, branding, banding, and printing, there still is a need to provide a way to even more uniquely identify whether the drug product within the dosage form is still viable while accomplishing this in a very unique, economical, and simplified manner.

In addition, growing demand for patient-friendly drug delivery forms has also increased interest in aseptic prefilled systems, such as pre-filled syringes. Pre-filled dosage forms reduce the risk of misidentification, dosage error and contamination. Additionally, pre-filled dosage forms eliminate container overfill that can be associated with vials. This is important when the product is in short supply, such as a vaccine. However, switching to a prefilled syringe presents its own set of challenges for manufacturers. In a prefilled syringe, a drug is exposed to materials it does not encounter in a vial. For example, lubrication is of limited importance in a stopper for a vial. In syringes, however, lubricity is essential to proper functioning of the device. The plunger must move smoothly and easily. Silicone is often used to ensure lubricity. Determining how silicone will interact with a given drug's stability and aggregation is a problem for both formulators and fillers. The current invention addresses these problems.

Finally, the need for quality monitoring in supply chain management of dosage forms is becoming increasingly important. Cold Chain refers to a subset of the total supply chain involving the production, storage, and distribution of drug products that require some level of temperature control in order to retain the drugs key characteristics and properties. The most critical portion of cold chain management is the distribution phase of drugs to the end-user (i.e. patient). The Food and Drug Administration requires that these drug products be stored under appropriate conditions so that their identity, strength, quality, effectiveness, and purity are not affected. However, many variables affect these properties, such as facility temperature deviation, airflow, air quality, duration of storage, container integrity, and seasonal considerations. Currently, quality is monitored on a destination-by-destination method.

The aforementioned background shows that a fundamental change is needed in the way quality is monitored for pharmaceutical formulations and dosage forms from the point of packaging until the time the drug reaches the end user. The present invention addresses these problems.

SUMMARY OF THE INVENTION

The invention provides for nanomaterials with functional characteristics that can be interfaced with pharmaceutical dosage forms. Specifically, nanomaterials fabricated to dosage forms that monitor the quality of the drug product enclosed therein. The nanomaterials can be designed to monitor a plurality of properties including but not limited to pH, temperature, potency, phase transition, solubility, particle size, polymorphisms, leachates, or any property (chemical or physical) that effects the activity or the drug product. As used herein, the term "drug" is synonymous with "pharmaceutical". In certain embodiments, the nanomaterial is fabricated to an encapsulated dosage form and quality is monitored to ensure purity and consistency of a pharmaceutical formulation.

In one embodiment, the nanomaterial is fabricated to a pre-filled syringe dosage form and quality is monitored to ensure potency of a vaccine.

In a further embodiment, the nanomaterial is fabricated to a dosage form enclosing an emulsion and phase transition is monitored to ensure proper efficacy at the time of use.

In a further embodiment, the nanomaterial is fabricated to a dosage form set forth in Table I.

The invention further comprises methods of fabricating a nanomaterial into a dosage form.

The invention further comprises methods of fabricating a nanomaterial into a dosage form set forth in Table I.

The invention further comprises methods of monitoring quality of a drug product enclosed within a dosage form fabricated with nanomaterials.

In a further embodiment, the invention provides for a method of monitoring quality of a drug product whereby the dosage form comprises a nanomaterial fabricated into the dosage form and whereby the monitoring occurs from packaging to distribution.

In a further embodiment, the invention provides for a method of monitoring quality of a drug product whereby the dosage form comprises a nanomaterial fabricated into the dosage form and whereby the monitoring occurs from distribution to wholesale.

In a further embodiment, the invention provides for a method of monitoring quality of a drug product whereby the dosage form comprises a nanomaterial fabricated into the dosage form and whereby the monitoring occurs from wholesale to retail.

In a further embodiment, the invention provides for a method of monitoring quality of a drug product whereby the dosage form comprises a nanomaterial fabricated into the dosage form and whereby the monitoring occurs from retail to the end user.

In a further embodiment, the invention provides for a method of monitoring quality of a drug product in a cold chain whereby the dosage form comprises a nanomaterial fabricated into the dosage form and whereby the temperature monitoring occurs from packaging to the end user.

In a further embodiment, the inventions comprises a dosage form fabricated with a nanomaterial whereby said dosage form encloses a drug product and whereby said nanomaterial monitors quality of said drug product.

BRIEF DESCRIPTION OF THE FIGURES

FIG. 1. Nanomaterial with Thermal Conductivity Properties Fabricated in Sheet Form. Nanomaterial is functionalized with the property of thermal conductivity. Organic matrix comprising polyhedral oligomeric silsequioxane ("POSS"). Particle size is between the range of about 10 nm and about 130 nm. Thermally conductive filler is used to reinforce nanomaterial. Nanomaterial is fabricated into a sheet with flat surface whereby the sheet interfaces a drug product and monitors the temperature of the drug product via a thermal biosensor.

FIG. 2. Thermal Interface Pad Fabricated in a pre-Filled Syringe to Monitor Temperature of a Vaccine. The thermal pad is interfaced with the drug product enclosed within the pre-filled syringe. The thermal pad is operably linked to a thermal biosensor to monitor temperature of the vaccine. Thermal biosensor is pre-set to "Cool" (i.e. Between 8° and 15° C. (46° and 59° F.)). Identification schema alerts end user when temperature is outside of pre-set condition.

FIG. 3. Monitoring and Detection Schema Using Nanomaterials with Enhanced Luminescence. Nanomaterials with enhanced luminescence properties are made using methods known in the art. The nanomaterial is fabricated into a dosage form to monitor quality of the drug product enclosed therein. A pre-determined schema will show when quality parameters fall outside the scope of the pre-set parameters. The schema displays a wide variety of displays. FIG. 3A. Shows the schema of changing colors. FIG. 3B. Shows the schema of symbol display. FIG. 3C. Shows the schema of word display.

FIG. 4. Nanomaterials with Enhanced Optical Properties Fabricated with Pharmaceutical Dosage Forms. Nanomaterial is functionalized with enhanced optical properties. A Graded Index Lens ("GRIN") is fabricated using a polymer/nanocrystal blend using methods known in the art. The GRIN lens has uniform thickness to provide for maximum interface with the dosage form and the optical fiber. The contact sensor is fabricated with a pharmaceutical dosage form.

FIG. 5. Optical Contact Sensor Fabricated into Dosage Form to Monitor Phase Transition of Emulsion. Contact sensor is fabricated into a dosage form and monitors phase transition of an emulsion. Upon an event taking a pre-determined quality parameter outside the quality protocol an end-user visually identifies the phase transition as outside the quality parameters.

FIG. 6. Schematic of Supply Chain Distribution in Drug Packaging. Once final formulation is determined the drug product is packaged using the fabricated dosage forms described herein. The dosage forms travel from packaging to distribution to wholesale to doctors or retail or hospitals and then to the end-user. The fabricated dosage forms monitor pre-set quality parameters and if an event takes the quality parameters outside the scope of the pre-set parameters the end-user is notified by a pre-set schema. Note, the supply chain can include several different configurations.

DETAILED DESCRIPTION OF THE INVENTION

Outline of Sections
I.) Definitions
II.) Nanomaterial
  a. Functional Properties of Nanomaterial
    i. Nanomaterial with thermal Conductivity
    ii. Nanomaterial with Porosity/Permeability
    iii. Nanomaterial with enhanced luminescence
    iv. Nanomaterial with enhanced acoustics
    v. Nanomaterial with magnetic properties
    vi. Nanomaterial with enhanced solubility
    vii. Shape Engineered nanomaterials
    viii. Nanomaterials with enhanced optical properties
III.) Sensors
IV.) Pharmaceutical Formulations
V.) Pharmaceutical Dosage Forms
VI.) Routes of Administration
VII.) Supply Chain Management
VIII.) KITS/Articles of Manufacture

I.) Definitions

Unless otherwise defined, all terms of art, notations and other scientific terms or terminology used herein are intended to have the meanings commonly understood by those of skill in the art to which this invention pertains unless the context clearly indicates otherwise. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art.

As used herein the terms "drug" and "pharmaceutical" include veterinary drugs and human drugs, including human biological drug products.

"Nanomaterial" means a material in any dimensional form (zero, one, two, three) and domain size less than 100 nanometers.

"Nanostructure" means a structure having at least one dimension that is less than 500 nanometers. Examples, include but are not limited to nanocrystals, nanocomposites, nanograins, nanotubes, nanoceramics, and nanopowders.

"nanocrystal" means nanostructures that are substantially monocrystalline. A nanocrystal has at least one region or characteristic dimension with a dimension of less than about 500 nm, and down to on the order of less than about 1 nm. As used herein, when referring to any numerical value, "about" means a value of .+-.10% of the stated value (e.g. about 100 nm encompasses a range of sizes from 90 nm to 110 nm, inclusive). The terms "nanocrystal," "nanodot," "dot" and "quantum dot" are readily understood by the ordinarily skilled artisan to represent like structures and are used herein interchangeably. The present invention also encompasses the use of polycrystalline or amorphous nanocrystals.

"aspect ratio" means the ratio of the maximum to the minimum dimension of a particle.

"biomaterial" (a.k.a. biological material) may refer to biological matter, biomass, biomolecule, and organic material (i.e. derived from living things or containing carbon).

"Integrated circuits (IC)" means a miniaturized electronic circuit that has been manufactured in the surface of a thin substrate of semiconductor material.

"hybrid integrated circuit" means a miniaturized electronic circuit bonded to a substrate or circuit board.

"nanowire" means a wire of dimensions of the order of a nanometer ($10^{-9}$ meters). Alternatively, nanowires can be defined as structures that have a lateral size constrained to tens of nanometers or less and an unconstrained longitudinal size. Nanowires include metallic (e.g., Ni, Pt, Au), semiconducting (e.g., InP, Si, GaN, etc.), and insulating (e.g., $SiO_2$, $TiO_2$). Molecular nanowires are composed of repeating molecular units either organic (e.g. DNA) or inorganic (e.g. $Mo_6S_{9-x}I_x$). "domain size" means the minimum dimension of a particular material morphology. In the case of powders, the domain size is the grain size. In the case of whiskers and fibers, the domain size is the diameter. In the case of plates and films, the domain size is the thickness.

"nanopowder" (a.k.a. "nanosize powders," "nanoparticles," and "nanoscale powders") means and refer to fine powders that have a mean size less than 250 nanometers. For example, in some embodiments, the nanopowders are powders that have particles with a mean domain size less than 100 nanometers and with an aspect ratio ranging from 1 to 1,000,000. Pure powders, as the term used herein, are powders that have composition purity of at least 99.9% by metal basis. For example, in some embodiments the preferred purity is 99.99%.

"Powder" (a.k.a. "powder", "particle", and "grain") are used interchangeably and encompass oxides, carbides, nitrides, borides, chalcogenides, halides, metals, intermetallics, ceramics, polymers, alloys, and combinations thereof. These terms include single metal, multi-metal, and complex compositions. These terms further include hollow, dense, porous, semi-porous, coated, uncoated, layered, laminated, simple, complex, dendritic, inorganic, organic, elemental, non-elemental, composite, doped, undoped, spherical, non-spherical, surface functionalized, surface non-functionalized, stoichiometric, and non-stoichiometric forms or substances. Further, the term powder in its generic sense includes one-dimensional materials (fibers, tubes, etc.), two-dimensional materials (platelets, films, laminates, planar, etc.), and three-dimensional materials (spheres, cones, ovals, cylindrical, cubes, monoclinic, parallelolipids, dumbbells, hexagonal, truncated dodecahedron, irregular shaped structures, etc.). The term metal used above includes any alkali metal, alkaline earth metal, rare earth metal, transition metal, semi-metal (metalloids), precious metal, heavy metal, radioactive metal, isotopes, amphoteric element, electropositive element, cation-forming element, and includes any current or future discovered element in the periodic table.

"Precursor" means any raw substance that can be transformed into a powder of same or different composition. In certain embodiments, the precursor is a liquid. The term precursor includes, but is not limited to, organometallics, organics, inorganics, solutions, dispersions, melts, sols, gels, emulsions, or mixtures.

"nanofiller" (a.k.a. nanostructured filler) means a structure or particle intimately mixed with a matrix to form a nanostructured composite. At least one of the nanostructured filler and the nanostructured composite has a desired material property which differs by at least 20% from the same material property for a micron-scale filler or a micron-scale composite, respectively. The desired material property is selected from the group consisting of refractive index, transparency to light, reflection characteristics, resistivity, permittivity, permeability, coercivity, B—H product, magnetic hysteresis, breakdown voltage, skin depth, curie temperature, dissipation factor, work function, band gap, electromagnetic shielding effectiveness, radiation hardness, chemical reactivity, thermal conductivity, temperature coefficient of an electrical property, voltage coefficient of an electrical property, thermal shock resistance, biocompatibility and wear rate. The nanostructured filler may comprise one or more elements selected from the s, p, d, and f groups of the periodic table, or it may comprise a compound of one or more such elements with one or more suitable anions, such as aluminum, antimony, boron, bromine, carbon, chlorine, fluorine, germanium, hydrogen, indium, iodine, nickel, nitrogen, oxygen, phosphorus, selenium, silicon, sulfur, or tellurium. The matrix may be a polymer (e.g., poly(methyl methacrylate), poly(vinyl alcohol), polycarbonate, polyalkene, or polyaryl), a ceramic (e.g., zinc oxide, indium-tin oxide, hafnium carbide, or ferrite), or a metal (e.g., copper, tin, zinc, or iron). Loadings of the nanofiller may be as high as 95%, although loadings of 80% or less are preferred. The invention also comprises devices which incorporate the nanofiller (e.g., electrical, magnetic, optical, biomedical, and electrochemical devices).

"coating" (a.k.a. "film", "laminate", or "layer") means any deposition comprising submicron and nanoscale powders. The term includes in its scope a substrate, surface, deposition, or a combination thereof having a hollow, dense, porous, semi-porous, coated, uncoated, simple, complex, dendritic, inorganic, organic, composite, doped, undoped, uniform, non-uniform, surface functionalized, surface non-functionalized, thin, thick, pretreated, post-treated, stoichiometric, or non-stoichiometric form or morphology.

"agglomerated" means a powder in which at least some individual particles of the powder adhere to neighboring particles, primarily by electrostatic forces.

"aggregated" means a powder in which at least some individual particles are chemically bonded to neighboring particles.

"supramolecular electronics" means the assemblies of pi-conjugated systems on the 5 to 100 nanometer length scale that are prepared by self-assembly with the aim to fit these structures between electrodes.

"biosensor" means a device for the detection of an analyte that combines a biological component with a physicochemical detector component. A biosensor comprises three parts: (i) a sensitive biological element (i.e. biological material, including but not limited to, tissue, microorganisms, organelles, cell receptors, enzymes, antibodies, nucleic acids, amino acids, etc.) or a biologically derived material or biomimic; (ii) a transducer; (iii) a detector element (i.e. chemical, physiochemical, optical, piezoelectric, electrochecmical; thermometric, or magnetic).

"optical biosensor" means a biosensor that utilizes the behavior and properties of light and the interaction of light with matter as the detector element.

"optical switch" means a switch that enables signals in optical fibers or integrated optical circuits (IOCs) to be selectively switched from one circuit to another.

"interface" means the boundary between two or more entities.

"pi-conjugated systems" (a.k.a. "stacking") means the noncovalent interaction between organic compounds containing aromatic moieties. $\pi$-$\pi$ interactions are caused by intermolecular overlapping of p-orbitals in $\pi$-conjugated systems, so they become stronger as the number of $\pi$-electrons increases.

"quantum dots" means a semiconductor nanostructure that confines the motion of conduction band electrons, valence band holes, or excitons (pairs of conduction band electrons and valence band holes) in all three spatial directions. The confinement can be due to electrostatic potentials (generated by external electrodes, doping, strain, impurities), due to the presence of an interface between different semiconductor materials (e.g. in the case of self-assembled quantum dots), due to the presence of the semiconductor surface (e.g. in the case of a semiconductor nanocrystal), or due to a combination of these. A quantum dot has a discrete quantized energy spectrum.

"molecular self-assembly" means the assembly of molecules without guidance or management from an outside source.

"nanocomposite" means materials that are created by introducing nanoparticulates into a macroscopic sample material. The nanomaterials add to the electrical and thermal conductivity as well as to the mechanical strength properties of the original material. In general, the nanomaterial used are carbon nanotubes and they are dispersed into the other composite materials during processing. The percentage by weight of the nanomaterials introduced is able to remain very low (on the order of 0.5%-5%) due to the incredibly high surface area to volume ratio of the particles.

"molecular electronics" (a.k.a. moletronics) means an interdisciplinary themed materials science in which the unifying feature is the use of molecular building blocks for the fabrication of electronic components, both passive (e.g. resistive wires) and active (e.g. transistors). Molecular electronics provides a means to extend Moore's Law beyond the foreseen limits of small-scale conventional silicon integrated circuits.

"Moore's law" means the empirical observation made in 1965 that the number of transistors on an integrated circuit for minimum component cost doubles every 24 months. It Is attributed to Gordon E. Moore (born 1929), a co-founder of Intel.

"supramolecular chemistry" means the area of chemistry which focuses on the noncovalent bonding interactions of molecules. Traditional organic synthesis involves the making and breaking of covalent bonds to construct a desired molecule.

"molecular recognition" means a chemical event in which a host molecule is able to form a complex with a second molecule (i.e. the guest). This process occurs through noncovalent chemical bonds, including but not limited to, hydrogen bonding, hydrophobic interactions, ionic interaction.

"static molecular recognition" means a 1:1 type complexation reaction between a host molecule and a guest molecule (an analogy is the interaction between a key and a keyhole.) To achieve advanced static molecular recognition, it is necessary to make recognition sites that are specific for guest molecules.

"dynamic molecular recognition" means a reaction that dynamically changes the equilibrium to an n:m type host-guest complex by a recognition guest molecule. Dynamic molecular recognition appearing in supermolecules is essential for designing highly functional chemical sensors and molecular devices.

"rotaxane" means a mechanically-interlocked molecular architecture consisting of a dumbbell-shaped molecule that is threaded through a macrocycle or ring-like molecule. The two components are kinetically trapped as the two end-groups of the dumbbell (often called stoppers) are larger than the internal diameter of the ring, and thus prevent dissociation (unthreading) since this would require significant distortion of the covalent bonds. The name, rotaxane, is derived from the Latin for wheel (rota) and axle (axis).

"synthetic molecular motors" means nanoscale devices capable of rotation under energy input. The basic requirements for a synthetic motor are repetitive 360° motion, the consumption of energy, and unidirectional rotation. Examples include but are not limited to triptycence motors and helicene.

"bar code" means a code representing characters by sets of parallel bars of varying thickness and separation that are read optically by transverse scanning.

"calibration" means ensuring continuous adequate performance of sensing, measurement, and actuating equipment with regard to specified accuracy and precision requirements.

"certification" means technical evaluation, made as part of and in support of the accreditation process that establishes the extent to which a particular computer system or network design and implementation meet a pre-specified set of requirements.

"validation" means establishing documented evidence which provides a high degree of assurance that a specific process will consistently produce a product meeting its predetermined specifications and quality attributes.

"Batch" means a specific quantity of a drug or other material that is intended to have uniform character and quality, within specified limits, and is produced according to a single manufacturing order during the same cycle of manufacture.

"Component" means any ingredient intended for use in the manufacture of a drug product, including those that may not appear in such drug product.

"Drug product" means a final formulation that contains an active drug ingredient generally, but not necessarily, in association with inactive ingredients. The term also includes a finished dosage form that does not contain an active ingredient but is intended to be used as a placebo.

"Active ingredient" means any component that is intended to furnish pharmacological activity or other direct effect in the diagnosis, cure, mitigation, treatment, or prevention of disease, or to affect the structure or any function of the body of man or other animals. The term includes those components that may undergo chemical change in the manufacture of the drug product and be present in the drug product in a modified form intended to furnish the specified activity or effect.

"Inactive ingredient" means any component other than an active ingredient.

"In-process material" means any material fabricated, compounded, blended, or derived by chemical reaction that is produced for, and used in, the preparation of the drug product.

"Lot number, control number, or batch number" means any distinctive combination of letters, numbers, or symbols, or any combination thereof, from which the complete history of the manufacture, processing, packing, holding, and distribution of a batch or lot of drug product or other material can be determined.

"Quality control unit" means any person or organizational element designated by the firm to be responsible for the duties relating to quality control.

"Acceptance criteria" means the product specifications and acceptance/rejection criteria, such as acceptable quality level and unacceptable quality level, with an associated sampling plan, that are necessary for making a decision to accept or reject a lot or batch.

"Process analytical technology" (a.k.a. PAT) means a mechanism to design, analyze, and control pharmaceutical manufacturing processes through the measurement of critical process parameters and quality attributes.

"New molecular entity" (a.k.a. NME or New Chemical Entity ("CNE")) means a drug that contains no active moiety that has been approved by FDA. An active moiety means the molecule or ion, excluding those appended portions of the molecule that cause the drug to be an ester, salt (including a salt with hydrogen or coordination bonds), or other non-covalent derivative (such as a complex, chelate, or clathrate) of the molecule, responsible for the physiological or pharmacological action of the drug substance.

"pH" means is a measure of the activity of hydrogen ions ($H^+$) in a solution and, therefore, its acidity.

"Encapsulation" means a range of techniques used to enclose medicines in a relatively stable shell, allowing them to, for example, be taken orally or be used as suppositories. The two main types of capsules are hard-shelled capsules, which are normally used for dry, powdered ingredients, and soft-shelled capsules, primarily used for oils and for active ingredients that are dissolved or suspended in oil. Both of these classes of capsule are made both from gelatine and from plant-based gelling substances like carrageenans and modified forms of starch and cellulose.

"Route of administration" means the path by which a drug product, fluid, poison, or other substance is brought into contact with the body.

"Pharmaceutical formulation" means the process in which different chemical substances are combined to a pure drug substance to produce a final drug product.

"Dosage form" means the physical form of a dose of a drug product, such as a capsule or injection. The route of administration is dependent on the dosage form of a given drug. Examples of dosage forms of the invention are set forth in Table I.

"Excipient" means an inactive substance used as a carrier for the active ingredients in a drug such as vaccines. Excipients are also sometimes used to bulk up formulations with very potent active ingredients, to allow for convenient and accurate dosage. Examples of excipients, include but are not limited to, antiadherents, binders, coatings, disintegrants, fillers, dilutents, flavors, colors, lubricants, and preservatives.

"Vehicle" means the excipients or matrix in which the active ingredient is prepared (e.g., normal saline).

"Potency" means substantively, the strength of a drug (i.e. vaccine) but more complex. It is not a factor proportional to the concentration of the active ingredient (antigen) but rather to the immunogenicity of the drug product (formulated antigen). So, just saying there is 300 mg of gp120 or 1 mg of DNA there in the vial isn't sufficient, the question is "is it immunogenic"? For a background on potency testing of vaccines, See, Habig, Veterinary Microbiology, 37:343-51: 1993. It concludes that a potency test should be reasonably predicative of efficacy in humans, i.e., measure a parameter that correlates with efficacy. Another important aspect to remember is that it should be sufficiently quantitative, so that it can be determined if your vaccine has lost 30%, 50%, or 70% potency, for example.

"Bulk" (a.k.a. Drug Substance) means the drug substance or the drug product which has not been filled into final containers for distribution. Final formulated bulk generally refers to drug product which is formulated and being stored or held prior to filling. Drug substance may be stored or held as "bulk" or "concentrated bulk" prior to formulation into drug product.

II.) Nanomaterial

The present invention provides for nanomaterials which are manufactured to achieve a desired function or property that will assist in the packaging of drug products. Nanomaterials of the inventions comprise nanostructures, nanocrystals, nanowires, nanotubes, nanofillers, nanocomposites, and precursors or any combination thereof. The nanomaterials useful in the present invention can also further comprise ligands conjugated, cooperated, associated or attached to their surface as described throughout. Suitable ligands include any group known to those skilled in the art. Use of such ligands can enhance the ability of the nanocrystals to incorporate into various solvents and matrixes, including polymers. Increasing the miscibility (i.e., the ability to be mixed without separation) of the nanocrystals in various solvents and matrixes allows them to be distributed throughout a polymeric composition such that the nanocrystals do not aggregate together and therefore do not scatter light. Such ligands are described as "miscibility-enhancing" ligands herein.

In a further embodiment, the invention provides polymeric layers comprising a polymer and nanocrystals embedded within the polymer, such that the layers act as photon-filtering nanocomposites. Suitably, the nanocrystals will be prepared from semiconductor materials, but any suitable material described throughout can be used to prepare the nanocrystals. In certain embodiments, the nanocrystals will have a size and a composition such that the nanocrystals absorb light of a particular wavelength or over a range of wavelengths. As such, the nanocrystals utilized in these embodiments are tailored such that their absorption characteristics are enhanced or maximized, while their emission characteristics are minimized, i.e. they will absorb light in a highly efficient manner, but suitably will emit only a very low level, or preferably no light. In other embodiments, however, the photon-filtering nanocomposites can also comprise nanocrystals that have high emission properties and emit light at a particular wavelength as discussed throughout. As such, the present invention provides nanocomposites that comprise different types of nanocrystals such that the nanocomposites exhibit several, or all, of the properties discussed throughout, in a layer. In embodiments of the present invention where the photon-filtering polymeric layers are used to coat pharmaceutical dosage forms, such dosage forms can be refractive (e.g., lenses) or reflective (e.g., mirrors).

Additionally, in certain embodiments of the present invention where the photon-filtering polymeric layers are used to encapsulate drug products, such drug products can be enclosed in any dosage form known to the skilled artisan.

By controlling the size and composition of the nanocrystals used in the practice of the present invention, the nanocrystals will absorb light of a particular wavelength, or a particular range of wavelengths, while not scattering light. The ability to make nanocrystals out of different semiconductors, and control their size, allows for pharmaceutical dosage forms to be fabricated with nanocrystals that will absorb light from the UV, to visible, to near infrared (NIR), to infrared (IR) wavelengths. Nanocrystals for use in the present invention will suitably be less than about 100 nm in size, and down to less than about 2 nm in size. In suitable embodiments, the nanocrystals of the present invention absorb visible light. As used herein, visible light is electromagnetic radiation with wavelengths between about 380 and about 780 nanometers that is visible to the human eye. Visible light can be separated into the various colors of the spectrum, such as red, orange, yellow, green, blue, indigo and violet. The photon-filtering nanocomposites of the present invention can be constructed to absorb light that makes up any one or more of these colors. For example, the nanocomposites of the present invention can be constructed to absorb blue light, red light, or green light, combinations of such colors, or any colors in between. As used herein, blue light comprises light between about 435 nm and about 500 nm, green light comprises light between about 520 nm and 565 nm and red light comprises light between about 625 nm and about 740 nm in wavelength. One of ordinary skill will be able to construct nanocomposites that can filter any combination of these wavelengths, or wavelengths between these colors, and such nanocomposites are embodied by the present invention.

As disclosed herein, the nanocrystals useful in the practice of the present invention can have a composition and a size such that they absorb light at a particular wavelength(s) and emit at a particular wavelength(s). In certain embodiments, the dosage forms of the present invention can comprise combinations of nanocrystals that function in the various ways described herein: For example, a nanocomposite of the present invention can comprise nanocrystals having specific, enhanced emission properties, others having specific, enhanced absorption properties but low emission properties, and the entire nanocomposite can be constructed such that the layer has a specific refractive index that is matched or tailored for a specific purpose. Combined in such a way, the pharmaceutical dosage forms of the present invention can be used as encapsulates for drug products (e.g. biologics, vaccines and injectables, blood products, diagnostic products, antibiotics, anti-inflammatory medicines etc.).

In preferred embodiments, it is desirable that the nanocrystals do not aggregate. That is, that they remain separate from each other in the dosage form and do not coalesce with one another to form larger aggregates. This is important, as individual crystals will not scatter light passing through the layer, while larger aggregated structures can create an opaque layer that can hinder the passage of light. However, depending on the parameters and individual specifications of the dosage form in which the nanomaterials are used the degree of aggregation may need to be modified to achieve the desired result.

Dispersion of nanocrystals into the drug product can be controlled by minimizing phase separation and aggregation that can occur when interfacing (physical) the nanocrystals with the drug product. A basic strategy known in the art is to design a 3-part ligand, in which the head-group, tail-group and middle/body-group can each be independently fabricated and optimized for their particular function, and then combined into an ideally functioning complete surface ligand. In on embodiment, the head group is selected to bind specifically to the material of the nanocrystal (or nanocrystal dosage form as the case may be). In one embodiment, the tail group is designed to interact strongly with the drug product and be miscible in the solvent utilized (and can, optionally, contain a linker group to the drug product) to allow maximum miscibility and loading density in the drug product without nanocrystal aggregation. In one embodiment, the middle or body group is selected for specific electronic functionality (e.g., charge isolation, Input/output, detector, etc.).

In another aspect of the invention nanomaterials comprise nanowires. While the example implementations described herein principally use Si, other types of nanowires (and other nanostructures such as nanoribbons, nanotubes, nanorods and the like) can be used including semiconductive nanowires, that are comprised of semiconductor material selected from, e.g., Si, Ge, Sn, Se, Te, B, C (including diamond), P, B—C, B—P(BP6), B—Si, Si—C, Si—Ge, Si—Sn and Ge—Sn, SiC, BN/BP/BAs, AlN/AlP/AlAs/AlSb, GaN/GaP/GaAs/GaSb, InN/InP/InAs/InSb, BN/BP/BAs, AlN/AlNAlAs/AlSb, GaN/GaP/GaAs/GaSb, InN/InP/InAs/InSb, ZnO/ZnS/ZnSe/ZnTe, CdS/CdSe/CdTe, HgS/HgSe/HgTe, BeS/BeSe/BeTe/MgS/MgSe, GeS, GeSe, GeTe, SnS, SnSe, SnTe, PbO, PbS, PbSe, PbTe, CuF, CuCl, CuBr, CuI, AgF, AgCl, AgBr, AgI, BeSiN2, CaCN2, ZnGeP2, CdSnAs2, ZnSnSb2, CuGeP3, CuSi2P3, (Cu, Ag) (Al, Ga, In, Tl, Fe)(S, Se, Te)2, Si3N4, Ge3N4, Al.sub.2O.sub.3, (Al, Ga, In)2(S, Se, Te)3, Al2CO, and an appropriate combination of two or more such semiconductors.

Additionally, the nanowires of the invention can include carbon nanotubes, or conductive or semiconductive organic polymer materials, (e.g., pentacene, and transition metal oxides).

In another aspect of the invention, nanomaterials of the invention comprise nanotubes. Nanotubes can be formed in combinations/thin films of nanotubes as is described herein for nanowires, alone or in combination with nanowires, to provide the properties and advantages described herein.

a: Functional Properties of Nanomaterials

In one aspect of the invention nanomaterials are fabricated to create a pharmaceutical dosage form (Table I). One of ordinary skill in the art will appreciate that the entire dosage form may comprise nanomaterials or the dosage form will consist of nanomaterials to achieve the desired functions described herein. In one embodiment, the nanomaterial is designed to include a functional property. The preferred functional property is one that provides a synergy with the dosage form and the drug product that the nanomaterial is being utilized in concert with. For example, nanomaterials may possess optical properties useful in detection of particulates or contaminates in gas or aerosols. This is particularly useful in monitoring the quality of inhalants that have been in storage for some time. In another example, a nanomaterial may possess thermal properties whereby deviations in temperature may be detected. This is particularly useful for drug products that are dependent on temperature for viability (i.e. vaccines, blood products).

A very wide variety of pure phase materials such as polymers are now readily known in the art. However, low cost pure phase materials are somewhat limited in the achievable ranges of a number of properties, including, for example, electrical conductivity, magnetic permeability, dielectric constant, and thermal conductivity. In order to circumvent these limitations, it has become common to form composites, in which a matrix is blended with a filler material with desirable properties.

In one embodiment, the invention comprises a nanofiller, intimately mixed with a matrix to form a nanostructured composite. At least one of the nanostructured filler and the nanostructured composite has a desired material property which differs by at least 20% from the same material property for a micron-scale filler or a micron-scale composite, respectively. The desired material property is selected from the group consisting of refractive index, transparency to light, reflection characteristics, resistivity, permittivity, permeability, coercivity, B—H product, magnetic hysteresis, breakdown voltage, skin depth, curie temperature, dissipation factor, work function, band gap, electromagnetic shielding effectiveness, radiation hardness, chemical reactivity, thermal conductivity, temperature coefficient of an electrical property, voltage coefficient of an electrical property, thermal shock resistance, biocompatibility and wear rate.

The nanofiller may comprise one or more elements selected from the s, p, d, and f groups of the periodic table, or it may comprise a compound of one or more such elements with one or more suitable anions, such as aluminum, antimony, boron, bromine, carbon, chlorine, fluorine, germanium, hydrogen, indium, iodine, nickel, nitrogen, oxygen, phosphorus, selenium, silicon, sulfur, or tellurium. The matrix may be a polymer (e.g., poly(methyl methacrylate), poly(vinyl alcohol), polycarbonate, polyalkene, or polyaryl), a ceramic (e.g., zinc oxide, indium-tin oxide, hafnium carbide, or ferrite), or a metal (e.g., copper, tin, zinc, or iron). Loadings of the nanofiller may be as high as 95%, although loadings of 80% or less are preferred. The invention also comprises devices which incorporate the nanofiller (e.g., electrical, magnetic, optical, biomedical, and electrochemical devices).

(i) Nanomaterial with Thermal Conductivity

In one aspect of the invention, the nanomaterial possesses the functional property of thermal conductivity. Any nanoparticle that can be functionalized and which has a higher thermal conductivity than the organic matrix can be used to prepare the present compositions. Suitable nanoparticles include but are not limited to colloidal silica, polyhedral oligomeric silsequioxane ("POSS"), nano-sized metal oxides (e.g. alumina, titania, zirconia), nano-sized metal nitrides (e.g. boron nitrides, aluminum nitrides) and nano-metal particles (e.g., silver, gold, or copper nanoparticles). In particularly useful embodiments, the nanoparticles are organo-functionalized POSS materials or colloidal silica. Colloidal silica exists as a dispersion of submicron-sized silica ($SiO_2$) particles in an aqueous or other solvent medium. The colloidal silica contains up to about 85 weight % of silicon dioxide ($SiO_2$) and typically up to about 80 weight % of silicon dioxide. The particle size of the colloidal silica is typically in a range between about 1 nanometers ("nm") and about 250 nm, and more typically in a range between about 5 nm and about 150 nm. The fillers used are micron-sized thermally conductive materials and can be reinforcing or non-reinforcing. In one embodiment, the present nanomaterial with thermal functionality can be formed into sheets and cut into any desired shape. In a preferred embodiment, the nanomaterials can advantageously be used for thermal interface pads and positioned on thermal biosensors. In a further embodiment, the thermal interface pad and thermal biosensor is fabricated into a pharmaceutical dosage form to monitor temperature of the drug product enclosed therein.

(ii) Nanomaterial with Porosity/Permeability

In one embodiment, nanomaterials possess predefined porosity and permeability properties. The properties are useful in the design of filters that are fabricated into pharmaceutical dosage forms. The filers can be used for such process as purification, etc. The nanomaterials are designed with a membrane or layer that is designed to block certain objects or substances while letting others through. The porosity/permeability properties of the nanomaterials can be used to separate liquids from liquids, solids from liquids, gas from liquids, or any combination of thereof. In a preferred embodiment, the porosity/permeability properties are designed to be advantageous to monitor the quality (such as purity, potency, etc.) of the drug product enclosed within the dosage form.

(iii) Nanomaterial with Enhanced Luminescence

In one embodiment, nanomaterials possess enhanced luminescent properties. The nanomaterials are made from nanopowders using standard methods known in the art. For example, luminescent nanomaterial is prepared using the following steps: forming a homogenized precursor solution of at least one lanthanide group metal precursor and at least one lanthanide series dopant precursor; adding a phosphate source and a fuel to the precursor solution; removing water from the precursor solution to leave a reaction concentrate; and igniting the reaction concentrate to form a powder comprising the plurality of nanoparticles. The nanomaterials of the invention can be used in pharmaceutical dosage form applications such as, display devices and imaging applications positioned on the pharmaceutical dosage form itself. In a preferred embodiment, the nanomaterials will be used in the quality monitoring of pharmaceutical dosage forms. In a further embodiment, the nanomaterial will display a predetermined schema when the quality of the pharmaceutical dosage form is outside the scope of the quality parameters set forth by the quality control protocol. It will be readily apparent to one of skill in the art that the schema can comprise a wide array of displays, including but not limited to, changing colors (including but not limited to red, blue, and green), displaying a symbol (e.g. and "X"), displaying a word (e.g. "EXPIRED").

(iv) Nanomaterial with Enhanced Acoustics

In one embodiment, nanomaterials possess enhanced acoustic functions. The nanomaterials are made from using standard methods known in the art. For example, a surface acoustic wave device fabricated on a lithium niobate substrate and a sensing bilayer positioned on the acoustic path of the surface acoustic wave device, the sensing bilayer further comprising nanocrystalline or other nanomaterial such as nanoparticles or nanowires of palladium and metal free phthalocyanine. Preferably, the surface acoustic wave device has a center frequency of about 200 MHz. Nanomaterials with enhanced acoustic properties will respond to gases (i.e. hydrogen, helium, etc.) in near real time, at low (room) temperature, without being affected by $CO_2$, $CH_4$ and other gases, in air ambient or controlled ambient, providing sensitivity to low ppm levels. In a preferred embodiment, the nanomaterials detect and monitor gases enclosed in pharmaceutical dosage forms described herein. In a further embodiment, the nanomaterial displays a predetermined schema when the quality of the pharmaceutical dosage form is outside the scope of the quality parameters set forth by the quality control protocol.

(v) Nanomaterial with Enhanced Magnetic Properties

In one embodiment, nanomaterials possess enhanced magnetic functions. The nanomaterials are made from using standards known in the art. For example, a solvent, preferably an ether or an aromatic solvent such as toluene, anisole, dioctylether, or the like, is added to a carboxylic acid, preferably Oleic acid, or the like. An amine, preferably Oleylamine or the like is then added to the solvent and Oleic acid solution to complete solution A. It will be appreciated that other solvents or amines not listed here may be used to perform the same decomposition. The solution A is added to a metal-organic precursor to form solution B. Solution B is then heated, for example by radiation at approximately 150 degrees C. in anisole for approximately 48 hours, under pressure, for example 3 Bars of H2. Nanorods begin to appear. The nanorods are crystalline hexagonal close packed (hcp), and grow along the c axis of the structure. The nanorods are in a thermodynamically stable form of cobalt after completion of the reaction. These thermodynamically stable cobalt nanorods will not rearrange into other forms such as spherical nanoparticles or any other form.

The nanoparticles that result from this embodiment exhibit magnetic properties, such as for example: i) saturation magnetization similar to the magnetic characteristics and properties of bulk cobalt; ii) enhanced magnetic anisotropy and strongly enhanced coercive magnetic field (as compared to bulk cobalt and spherical nanoparticles) due to the shape anisotropy. The nanomaterials with enhanced magnetic properties will allow particle orientation in magnetic fields to optimize high-frequency device applications. In a preferred embodiment, the high-frequency device is fabricated into a pharmaceutical dosage form.

(vi) Nanomaterial with Enhanced Solubility

In one embodiment, nanomaterials possess enhanced solubility properties. The nanomaterials are made from using standards known in the art. For example, a rigid poly(aryleneethynylene) polymer is coupled with a para-diethynyl-($R_1$-$R_x$)arylene and an ($R_1$-$R_y$)-para-dihaloarylene in the presence of a first polymerization-terminating haloaryl agent under conditions and for a period of time to produce fluorescence. Then terminating the coupling by addition of a second polymerization-terminating haloaryl agent, the second haloaryl agent having equal or greater activity for coupling as compared to the ($R_1$-$R_y$)-para-dihaloarylene. The nanomaterials with enhanced solubility will provide for functional nanomaterials that can be used for epoxy and engineering plastic composites, filters, actuators, adhesive composites, elastomer composites, materials for thermal management (interface materials, materials for heat transfer applications), improved dimensionally stable structures for sensors, optoelectronic or microelectromechanical components or subsystems, rapid prototyping materials, composite fibers, etc. In a preferred embodiment, the nanomaterial is fabricated in a pharmaceutical dosage form. In a further embodiment, the nanomaterial with enhanced solubility properties is used to monitor quality of the drug product enclosed within the pharmaceutical dosage form.

(vii) Shape Engineered Nanomaterials

In one embodiment, nanomaterials are engineered for specific shapes or mechanical properties. The nanomaterials are made from using standards known in the art. For example, nanomaterials are made with modified degree of agglomeration. Additionally, nanomaterials are made with a modified surface area. Additionally, nanomaterials are made with post-processing to modify the phase and shape. Additionally, post-processing is utilized to achieve consolidation. Nanomaterials that are shape engineered are used for ceramic, metal, or composite seals on pharmaceutical dosage forms. Additionally as filters with a defined porosity gradient, monitors, sensors, drug delivery devices, and biocatalysts from nanoscale powders using the multi-layer laminating process to produce three-dimensional shapes. In a preferred embodiment, the nanomaterials are used in pharmaceutical dosage forms. In a further embodiment, the nanomaterials monitor quality of drug products enclosed within the pharmaceutical dosage form.

(viii) Nanomaterials Will Enhanced Optical Properties

In one embodiment, nanomaterials are engineered with enhanced optical properties. The nanomaterials are made from using standards known in the art. Generally, in optical lenses, the optical path length varies with distance from its center, where optical path length is defined as the product of the physical path length, thickness, and the refractive index, n, of the lens material. In the most common lenses, the refractive index, n, is fixed and the thickness, varies. However, a lens can also be created by keeping the thickness, constant and varying the refractive index as a function of distance from the axis of the lens. Such a lens is called a Graded Index lens, or sometimes abbreviated as a GRIN lens. The methods of the present invention can also be used to create GRIN lenses. Polymer/nanocrystal blends can be used to make GRIN lenses due to the dramatic refractive index difference between nanocrystals (e.g., ZnS about 2.35) and optical plastics such as poly(methyl methacrylate) (PMMA) (refractive index about 1.45). With normal glass, a difference of about 0.05 refractive index units is achievable over about 8 mm. Utilizing the methods and processes of the present application, a difference of about 0.20 refractive index units over about 8 mm can be achieved to make much more powerful lenses. Nanomaterials with enhanced optical properties can be used for contact sensors, remote sensors, LIDAR, optical parametric oscillators, optical data storage, optical spectroscopy, optical amplifiers, wavelength translation devices, super sensitive optical detection, and optical switches. In a preferred embodiment, the sensors with enhanced optical properties are fabricated into pharmaceutical dosage forms. In a further embodiment, the optically enhanced nanomaterials are used to monitor quality of the drug products enclosed within the pharmaceutical dosage forms described herein.

III.) Sensors

In one embodiment, the invention relates to sensors that are fabricated into pharmaceutical dosage forms. In a preferred embodiment, the sensors are made from nanomaterials disclosed herein and are developed on a microscopic scale using MEMS (micro-electrical-mechanical-systems) technology. In one embodiment, the sensor is made from $1^{st}$ generation MEMS technology (i.e. a sensor element mostly based on a silicon or similar structure, sometimes combined with analog amplification on a nanomaterial). In one embodiment, the sensor is made from $2^{nd}$ generation MEMS technology (i.e. a sensor element combined with analog amplification and analog-to-digital converter on one nanomaterial). In a preferred embodiment, the sensor is made from $3^{rd}$ generation MEMS technology (i.e. fusion of the sensor element with analog amplification, analog-to-digital converter and digital intelligence for linearization and temperature compensation on the same nanomaterial). In another preferred embodiment, the sensor is made from $4^{th}$ generation MEMS technology (i.e. memory cells for calibration and temperature compensation data are added to the elements of the 3rd generation sensor). The advantages of using sensors made out of nanomaterials is the sensors can reach significantly higher speeds and sensitivity that macroscale sensors. In addition, the scale of the pharmaceutical dosage forms disclosed herein make use of nanosensors optimal.

It will be appreciated by one of skill in the art that the type of sensor needed will be a direct function to the pharmaceutical dosage form that is being used and the drug product that is being monitored. For example, monitoring the potency of a vaccine will require different monitoring parameters that monitoring the pH of an antibiotic which in turn will require different monitoring parameters that monitoring the temperature of a blood product. In these situations, it will be appreciated by one of ordinary skill that either (i) the same sensors can be used with different detecting criteria or (ii) different types of sensors can be used to achieve the best level of monitoring for a specific pharmaceutical dosage form.

Accordingly, sensors of the present invention comprise thermal, electromagnetic, mechanical, chemical, optical, radiation, acoustic, and biological sensors. In one embodiment, thermal sensors include but are not limited to thermometers, thermocouples, temperature sensitive resistors, bolometers, calorimeter.

In a further embodiment, electromagnetic sensors include but are not limited to ohmmeters, multimeters, galvanometers, ammeters, leaf electroscopes, watt-hour meters, magnetic compasses, fluxgate compasses, magnetometers, and metal detectors.

In a further embodiment, mechanical sensors include but are not limited to barometers, barographs, pressure gauges, air speed indicators, rate of change sensors, flow sensors, anemometers, flow meters, gas meters, water meters, mass flow sensors, acceleration sensors, whisker sensors, Quadrature wheels, and positions switches.

In a further embodiment, chemical sensors include but are not limited to oxygen sensors (a.k.a. $\lambda$ sensors), ion-selective electrodes, pH glass electrodes, and redox electrodes.

In a further embodiment, optical and radiation sensors include but are not limited to RADAR, LIDAR, dosimeters, particle detectors, scintillators, wire chambers, cloud chambers, bubble chambers, infrared sensors, photocells, photodiodes, phototransistors, image sensors; vacuum tube devices, and proximity sensors.

In a further embodiment, acoustic sensors include but are not limited to ultrasounds and SONAR.

In a further embodiment, biological sensors include but are not limited to biosensors that can detect physical aspects of the external environment such as light, motion, temperature, magnetic fields, gravity, humidity, vibration, pressure, electrical fields, and sound. Additionally, biosensors that can detect environmental molecules such as toxins, nutrients, and pheromones are within the scope of the invention. Additionally, biosensors that can detect metabolic parameters such as glucose level and oxygen level are within the scope of the invention.

In another aspect, this invention also includes a method of producing an improved sensor device. A non-stoichiometric nanopowder is sonicated in a solvent to form a slurry. The slurry is brushed onto screen-printed electrodes and allowed to dry at to remove the solvent. A dissolved polymer may also be included in the slurry. The screen-printed electrodes may be gold electrodes on an alumina substrate. The screen may be made from stainless steel mesh at least 8.times.10 inches in size, with a mesh count of 400, a wire diameter of 0.0007 inches, a bias of 45.degree., and a polymeric emulsion of 0.0002 inches.

In another aspect, this invention includes an improved sensor device prepared from a screen printable paste. A nanopowder and polymer are mechanically mixed; a screen-printing vehicle is added to the mixture and further mechanically mixed. The mixture is milled and screen-printed onto prepared electrodes. The paste is allowed to level and dry. This invention also includes the improved sensor devices produced by the above processes.

In another aspect of the invention, thermal sensors are prepared from nanostructured powders. These thermal sensors can be used to monitor aspects of the pharmaceutical manufacturing process including but not limited to monitor radiation, power, heat and mass flow, charge and momentum flow, and phase transformation.

In a preferred embodiment, the sensors disclosed herein are fabricated into a pharmaceutical dosage form whereby the dosage form comprise the nanomaterial or are fabricated to consist of 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% nanomaterial and the remaining ingredients of the specified dosage form are known in the art.

IV.) Pharmaceutical Formulation

Pharmaceutical formulation is the process in which different chemical substances are combined to a pure drug substance to produce a final drug product. Formulation studies involve developing a preparation of the drug which is both stable and acceptable to the patient. For orally taken drugs, this usually involves incorporating the drug into a tablet or a capsule. It is important to appreciate that a tablet contains a variety of other substances apart from the drug itself, and studies have to be carried out to ensure that the drug is compatible with these other substances.

An excipient is an inactive substance used as a carrier for the active ingredients of a drug product. In addition, excipients can be used to aid the process by which a drug product is manufactured. The active substance is then dissolved or mixed with an excipient. Excipients are also sometimes used to bulk up formulations with very potent active ingredients, to allow for convenient and accurate dosage. Once the active ingredient has been purified, it cannot stay in purified form for very long. In many cases it will denature, fall out of solution, or stick to the sides of the container. To stabilize the active ingredient, excipients are added to ensure that the active ingredient stays active, and is stable for a long enough period of time that the shelf-life of the product makes it competitive with other products and safe for the end-user. Examples of excipients, include but are not limited to, anti-adherents, binders, coatings, disintegrants, fillers, dilutents, flavors, colors, lubricants, and preservatives. The final formulation comprises and active ingedient and excipients which are then enclosed in the pharmaceutical dosage form.

Pre-formulation involves the characterization of a drug's physical, chemical, and mechanical properties in order to choose what other ingredients should be used in the preparation. Formulation studies then consider such factors as particle size, polymorphism, pH, and solubility, as all of these can influence bioavailability and hence the activity of a drug. The drug must be combined with inactive additives by a method which ensures that the quantity of drug present is consistent in each dosage unit (e.g. each tablet). The dosage should have a uniform appearance, with an acceptable taste, tablet hardness, or capsule disintegration.

It is unlikely that these studies will be complete by the time clinical trials commence. This means that simple preparations are developed initially for use in phase I clinical trials. These typically consist of hand-filled capsules containing a small amount of the drug and a diluent. Proof of the long-term stability of these formulations is not required, as they will be used (tested) in a matter of days. However, long-term stability is critical in supply chain management since the time the final formulation is packaged until it reaches the patient can be several months or years. In addition, the location of the patient in relation to the packaging of the drug product influences quality factors. Consideration has to be given to what is called the drug load (i.e. the ratio of the active drug to the total contents of the dose). A low drug load may cause homogeneity problems. A high drug load may pose flow problems or require large capsules if the compound has a low bulk density. By the time phase III clinical trials are reached, the formulation of the drug should have been developed to be close to the preparation that will ultimately be used in the market.

A knowledge of stability is essential by this stage, and conditions must have been developed to ensure that the drug is stable in the preparation. If the drug proves unstable, it will invalidate the results from clinical trials since it would be impossible to know what the administered dose actually was. Stability studies are carried out to test whether temperature, humidity, oxidation, or photolysis (ultraviolet light or visible light) have any effect, and the preparation is analysed to see if any degradation products have been formed. It is also important to check whether there are any unwanted interactions between the preparation and the container. If a plastic container is used, tests are carried out to see whether any of the ingredients become adsorbed on to the plastic, and whether any plasticizers, lubricants, pigments, or stabilizers leach out of the plastic into the preparation. Even the adhesives for the container label need to be tested, to ensure they do not leach through the plastic container into the preparation. The way a drug is formulated can avoid some of the problems associated with oral administration. Drugs are normally taken orally as tablets or capsules. The drug (active substance) itself needs to be soluble in aqueous solution at a controlled rate. Such factors as particle size and crystal form can significantly affect dissolution. Fast dissolution is not always ideal. For example, slow dissolution rates can prolong the duration of action or avoid initial high plasma levels.

Accordingly, in one embodiment, the nanomaterials of the invention are fabricated into the pharmaceutical dosage form whereby the nanomaterials are used to monitor quality of the drug product enclosed within the dosage form from the point of packaging until use by the end-user.

In a further embodiment, the nanomaterials of the invention are fabricated into a pharmaceutical dosage form whereby the nanomaterials are used to monitor pH levels of the drug product.

In a further embodiment, the nanomaterials of the invention are fabricated into a pharmaceutical dosage form whereby the nanomaterials are used to monitor temperature levels of the drug product.

In a further embodiment, the nanomaterials of the invention are fabricated into a pharmaceutical dosage form whereby the nanomaterials are used to monitor stability of the drug product.

In a further embodiment, the nanomaterials of the invention are fabricated into a pharmaceutical dosage form whereby the nanomaterials are used to monitor oxidation of the drug product.

In a further embodiment, the nanomaterials of the invention are fabricated into a pharmaceutical dosage form whereby the nanomaterials are used to monitor degradation of the drug product.

In a further embodiment, the nanomaterials of the invention are fabricated into a pharmaceutical dosage form whereby the nanomaterials are used to monitor leachates of the drug product.

In a further embodiment, the nanomaterials of the invention are fabricated into a pharmaceutical dosage form whereby the nanomaterials are used to monitor potency of the drug product.

In a further embodiment, the nanomaterials of the invention are fabricated into a pharmaceutical dosage form whereby the nanomaterials are used to monitor cold chain requirements of the drug product.

V.) Pharmaceutical Dosage Forms

A dosage form is the physical form of a dose of a drug product, such as a capsule or injection. Table I summarizes the generally recognized dosage forms. The route of administration (See, Section VI. Entitled "Route of Administration") is dependent on the dosage form of a given drug. Various dosage forms may exist for the same compound, since different medical conditions may warrant different routes of administration. For example, persistent vomiting may make it difficult to use an oral dosage form. In this case, it may be advisable to use either an injection or a suppository. Also, specific dosage forms may be warranted for certain medications, since there may be problems with stability (e.g. insulin cannot be given orally since it is digested by the stomach).

In the packaging of pharmaceuticals, encapsulation refers to a range of techniques used to enclose medicines in a relatively stable shell, allowing them to, for example, be taken orally or be used as suppositories. The two main types of capsules are hard-shelled capsules, which are normally used for dry, powdered ingredients, and soft-shelled capsules, primarily used for oils and for active ingredients that are dissolved or suspended in oil. Both of these classes of capsule are made both from gelatine and from plant-based gelling substances like carrageenans and modified forms of starch and cellulose.

Since their inception, capsules have been viewed as the medium of more potent medicines than tablets, which are more commonly associated with weaker over-the-counter drugs.

A tablet is usually a compressed preparation that contains, 5-10% of the drug (active substance); 80% of fillers, disintegrants, lubricants, glidants, and binders; and 10% of compounds which ensure easy disintegration, disaggregation, and dissolution of the tablet in the stomach or the intestine.

The disintegration time can be modified for a rapid effect or for sustained release. Special coatings can make the tablet resistant to the stomach acids such that it only disintegrates in the duodenum as a result of enzyme action or alkaline pH.

Pills can be coated with sugar, varnish, or wax to disguise the taste. Some tablets are designed with an osmotically active core, surrounded by an impermeable membrane with a pore in it. This allows the drug to percolate out from the tablet at a constant rate as the tablet moves through the digestive tract.

An injection is a method of putting liquid into the body with a hollow needle and a syringe which is pierced through the skin long enough for the material to be kneed into the body.

An emulsion is a mixture of two immiscible (unblendable) substances. One substance (the dispersed phase) is dispersed in the other (the continuous phase). Examples of emulsions include propofol, among others.

Emulsions tend to have a cloudy appearance, because the many phase interfaces scatter light that passes through the emulsion. Emulsions are unstable and thus do not form spontaneously. Energy input through shaking, stirring, homogenizers, or spray processes are needed to form an emulsion. Over time, emulsions tend to revert to the stable state of oil separated from water. Surface active substances can increase the kinetic stability of emulsions greatly so that, once formed, the emulsion does not change significantly over years of storage. This phenomenon is called coalescence, and happens when small droplets recombine to form bigger ones. Fluid emulsions can also suffer from creaming, the migration of one of the substances to the top of the emulsion.

Other types of non-limiting dosage forms within the scope of the present invention are set forth in Table I.

In one embodiment, the nanomaterials of the invention are fabricated into a pharmaceutical dosage form whereby the nanomaterials are used to monitor quality parameters of the drug product enclosed therein.

In a further embodiment, the nanomaterials of the invention are fabricated into a pharmaceutical dosage form set forth in Table I whereby the nanomaterials are used to monitor quality parameters of the drug product enclosed therein.

In a preferred embodiment, the nanomaterials disclosed herein are fabricated into a pharmaceutical dosage form set forth in Table I whereby the dosage form comprise the nanomaterial or are fabricated to consist of 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% nanomaterial and the remaining ingredients of the specified dosage form are known in the art.

VI.) Routes of Administration

A route of administration is the path by which a drug, fluid, or other substance is brought into contact with the body.

As one of ordinary skill in the art will appreciate, a substance must be transported from the site of entry to the part of the body where its action is desired to take place. However, using the body's transport mechanisms for this purpose can be far from trivial. The pharmacokinetic properties of a drug are critically influenced by the route of administration.

Routes of administration can broadly be divided into three categories. Topical, wherein a local effect is desired. A substance is applied directly where its action is desired. Enteral, wherein the desired effect is systemic (non-local). An example is a substance is given via the digestive tract. Parenteral, wherein the desired effect is systemic. A substance is given by other routes than the digestive tract (i.e. injection). Table II summarizes the general routes of administration.

VII.) Supply Chain Management

Proper supply chain management of packaged pharmaceuticals is critical to provide quality drugs to end-users. This includes monitoring traditional areas of supply chain to include packaging, product protection, storage, and distribution. In addition, monitoring the Cold Chain (i.e. a subset of the supply chain that require temperature control) in order to retain drugs key properties is vital. Specifically, from the point when the drug product is packaged until it reaches the end-user (See, FIG. 6). Depending on the geographic location of the end-user and circumstances surrounding the need for treatment (i.e. a natural disaster), this could take weeks, months, etc.

Additionally, not all cold chain products are the same and the need for monitoring temperature and other quality parameters differs for each type of drug product. Table III sets forth the generally recognized categories of temperatures in cold chain compliance. In addition, Table IV shows general consequences of what happens to drug products when cold chain management fails.

In one embodiment, the invention provides for a method of monitoring quality of a drug product whereby the dosage form comprises a nanomaterial fabricated into the dosage form and whereby the nanomaterial monitors the quality parameters set for the quality control unit.

In a further embodiment, the invention provides for a method of monitoring quality of a drug product whereby the dosage form comprises a nanomaterial fabricated into the dosage form and whereby the monitoring occurs from packaging to distribution (See, FIG. 6).

In a further embodiment, the invention provides for a method of monitoring quality of a drug product whereby the dosage form comprises a nanomaterial fabricated into the dosage form and whereby the monitoring occurs from distribution to wholesale (See, FIG. 6).

In a further embodiment, the invention provides for a method of monitoring quality of a drug product whereby the dosage form comprises a nanomaterial fabricated into the dosage form and whereby the monitoring occurs from wholesale to retail (See, FIG. 6).

In a further embodiment, the invention provides for a method of monitoring quality of a drug product whereby the dosage form comprises a nanomaterial fabricated into the dosage form and whereby the monitoring occurs from retail to the end user (See, FIG. 6).

In a preferred embodiment, the invention provides for a method of monitoring quality of a drug product in a cold chain whereby the dosage form comprises a nanomaterial fabricated into the dosage form and whereby the temperature monitoring occurs from packaging to the end user (See, FIG. 6).

VII.) Kits/Articles of Manufacture

For use in monitoring quality of drug products enclosed within pharmaceutical dosage forms (Table I) described herein, kits are within the scope of the invention. Such kits can comprise a carrier, package, or container that is compartmentalized to receive one or more containers such as boxes, shrink wrap, and the like, each of the container(s) comprising one of the separate elements to be used in the method, along with a program or insert comprising instructions for use, such as a use described herein.

The kit of the invention will typically comprise the container described above and one or more other containers associated therewith that comprise nanomaterials fabricated into pharmaceutical dosage forms desirable from a commercial and user standpoint, listing contents and/or instructions for use, and package inserts with instructions for use.

A program can be present on or with the container. Directions and or other information can also be included on an insert(s) or program(s) which is included with or on the kit. The program can be on or associated with the container.

The terms "kit" and "article of manufacture" can be used as synonyms.

The article of manufacture typically comprises at least one container and at least one program. The containers can be formed from a variety of materials such as glass, metal or plastic.

EXAMPLES

Various aspects of the invention are further described and illustrated by way of the several examples that follow, none of which is intended to limit the scope of the invention.

Example 1: Thermally Conductive Nanomaterials Fabricated into Pre-Filled Syringes The nanomaterial with enhanced thermal conductivity is generated by methods known in the art. The nanomaterial is formed into sheets providing an interface between the thermal pad and the drug product and providing an interface between the thermal pad and a thermal biosensor. (FIG. 1). In one embodiment, the nanomaterial is fabricated into a pre-filled syringe. The thermal biosensor monitors temperature of the drug product enclosed therein (e.g. a vaccine). When the temperature falls outside the pre-set parameter(s) a schema notifies the end-user (e.g. doctor, patient, nurse, etc.) and the dosage form is discarded or corrective action is taken. (FIG. 2).

In one embodiment, the monitoring and quality assessment achieves a step of supply chain management whereby drug product quality and shelf-life are increased. Costs are reduced over time.

In a further embodiment, the monitoring and quality assessment achieves a step of cold chain management whereby drug product quality and shelf-life are increased. Costs are reduced over time.

Example 2: Quality Monitoring of Drug Product Using Nanomaterials with Enhanced Luminescent Properties The nanomaterial with enhanced luminescent properties is generated by methods known in the art. Dosage forms fabricated with the nanomaterials are produced by standard methods and a drug product is enclosed therein. Sensors monitor such properties as pH, temperature, degradation, potency, solubility, and other properties affecting drug product efficacy. When the pre-set property falls outside the quality parameter(s) a schema notifies the end-user (e.g. doctor, patient, nurse, etc.) and the dosage form is discarded or corrective action is taken. In one embodiment, the schema comprises a color change in the dosage form. In one embodiment, the schema comprises a symbol display on the dosage form. In one embodiment, the schema comprises a word display on the dosage form. (FIG. 3).

Example 3: Optically Enhanced Nanomaterials Fabricated into Dosage Forms Enclosing Emulsions The nanomaterial with enhanced optical properties is generated by methods known in the art. The nanomaterial is formed into graded index lens whereby the thickness of the lens is uniform providing an optimal interface between the contact lens the dosage form and the optical fiber. (FIG. 4). In one embodiment, the nanomaterial is fabricated into a dosage form enclosing an emulsion.

An emulsion is a mixture of two or more immiscible (unblendable) substances. One substance (the dispersed phase) is dispersed in the other (the continuous phase).

Emulsions tend to have a cloudy appearance, because the many phase interfaces scatter light that passes through the emulsion. Emulsions are unstable and thus do not form spontaneously. Energy input through shaking, stirring, homogenizers, or spray processes are needed to form an emulsion. Over time, emulsions tend to revert to a stable state. Additionally, surface active substances can increase the kinetic stability of emulsions greatly so that, once formed, the emulsion does not change significantly over years of storage.

However, some emulsions are so unstable that they will quickly separate unless continuous energy is applied. Fluid emulsions can also suffer from creaming, the migration of one of the substances to the top of the emulsion under the influence of buoyancy.

Emulsions are part of a more general class of two-phase systems of matter called colloids. Although the terms colloid and emulsion are sometimes used interchangeably, emulsion tends to imply that both the dispersed and the continuous phase are liquid.

There are three types of emulsion instability, (i) flocculation, where the particles form clumps; (ii) creaming, where the particles concentrate towards the surface (or bottom, depending on the relative density of the two phases) of the mixture while staying separated; and (iii) breaking and coalescence where the particles coalesce and form a layer of liquid.

Accordingly, the contact lens monitors phase transformation of the emulsion enclosed within the dosage form. When the phase transition falls outside the pre-set parameter(s) the end-user (e.g. doctor, patient, nurse, etc.) provides a visual inspection and the dosage form is discarded or corrective action is taken. (FIG. 5).

In one embodiment, the monitoring and quality assessment achieves a step of supply chain management whereby drug product quality and shelf-life are increased. Costs are reduced over time.

In a further embodiment, the monitoring and quality assessment achieves a step of cold chain management whereby drug product quality and shelf-life are increased. Costs are reduced over time.

Example 4: Methods of Monitoring Quality of Drug Product Using Dosage Forms Fabricated with Nanomaterials The final formulation of the drug product is determined and is packaged using standards methods known in the art into dosage forms fabricated with nanomaterials. The dosage forms comprise a detection schema to notify end-users (doctors, patients, hospitals, etc.) when the drug product properties being monitored fall outside the quality protocol.

In one embodiment, the invention provides for a method of monitoring quality of a drug product whereby the dosage form comprises a nanomaterial fabricated into the dosage form and whereby the nanomaterial monitors the quality parameters set for the quality control unit.

In a further embodiment, the invention provides for a method of monitoring quality of a drug product whereby the dosage form comprises a nanomaterial fabricated into the dosage form and whereby the monitoring occurs from packaging to distribution (See, FIG. 6).

In a further embodiment, the invention provides for a method of monitoring quality of a drug product whereby the dosage form comprises a nanomaterial fabricated into the dosage form and whereby the monitoring occurs from distribution to wholesale (See, FIG. 6).

In a further embodiment, the invention provides for a method of monitoring quality of a drug product whereby the dosage form comprises a nanomaterial fabricated into the dosage form and whereby the monitoring occurs from wholesale to retail (See, FIG. 6).

In a further embodiment, the invention provides for a method of monitoring quality of a drug product whereby the dosage form comprises a nanomaterial fabricated into the dosage form and whereby the monitoring occurs from retail to the end user (See, FIG. 6).

In a preferred embodiment, the invention provides for a method of monitoring quality of a drug product in a cold chain whereby the dosage form comprises a nanomaterial fabricated into the dosage form and whereby the temperature monitoring occurs from packaging to the end user (See, FIG. 6). Table III shows generally recognized temperatures in cold chain compliance.

In one embodiment, the monitoring achieves a step of supply chain management whereby drug product quality and shelf-life are increased. Costs are streamlined over time.

The present invention is not to be limited in scope by the embodiments disclosed herein, which are intended as single illustrations of individual aspects of the invention, and any that are functionally equivalent are within the scope of the invention. Various modifications to the models and methods of the invention, in addition to those described herein, will become apparent to those skilled in the art from the foregoing description and teachings, and are similarly intended to fall within the scope of the invention. Such modifications or other embodiments can be practiced without departing from the true scope and spirit of the invention.

TABLE I

Types of Dosage Forms
Types of generally recognized Dosage Forms

AEROSOL
AEROSOL, FOAM
AEROSOL, METERED
AEROSOL, POWDER
AEROSOL, SPRAY
BAR, CHEWABLE
BEAD
BEAD, IMPLANT, EXTENDED RELEASE
BLOCK
CAPSULE
CAPSULE, COATED
CAPSULE, COATED PELLETS
CAPSULE, COATED, EXTENDED RELEASE
CAPSULE, DELAYED RELEASE
CAPSULE, DELAYED RELEASE PELLETS
CAPSULE, EXTENDED RELEASE
CAPSULE, FILM COATED, EXTENDED RELEASE
CAPSULE, GELATIN COATED
CAPSULE, LIQUID FILLED
CEMENT
CIGARETTE
CONE
CORE, EXTENDED RELEASE
CREAM
CRYSTAL
CULTURE
DENTIFRICE
DENTIFRICE/GEL
DIAPHRAGM
DISC
DOUCHE
DRESSING
ELIXIR
EMULSION
ENEMA
EXTRACT
FILM
FILM, EXTENDED RELEASE
FILM, SOLUBLE
GAS
GEL
GEL, JELLY
GENERATOR
GLOBULE
GRAFT
GRANULE
GRANULE, DELAYED RELEASE
GRANULE, EFFERVESCENT
GRANULE, FOR SOLUTION
GRANULE, FOR SUSPENSION
GRANULE, FOR SUSPENSION, EXTENDED RELEASE
GUM
GUM, CHEWING
GUM, RESIN
INHALANT
INJECTION
INJECTION, EMULSION

TABLE I-continued

Types of Dosage Forms
Types of generally recognized Dosage Forms

INJECTION, POWDER, FOR SOLUTION
INJECTION, POWDER, FOR SUSPENSION
INJECTION, POWDER, FOR SUSPENSION, EXTENDED RELEASE
INJECTION, POWDER, LYOPHILIZED, FOR LIPOSOMAL SUSPENSION
INJECTION, POWDER, LYOPHILIZED, FOR SOLUTION
INJECTION, POWDER, LYOPHILIZED, FOR SUSPENSION
INJECTION, POWDER, LYOPHILIZED, FOR SUSPENSION, EXTENDED RELEASE
INJECTION, SOLUTION
INJECTION, SOLUTION, CONCENTRATE
INJECTION, SUSPENSION
INJECTION, SUSPENSION, EXTENDED RELEASE
INJECTION, SUSPENSION, LIPOSOMAL
INSERT, EXTENDED RELEASE
INTRAUTERINE DEVICE
IRRIGANT
LINIMENT
LIPSTICK
LIQUID
LOLLIPOP
LOTION
LOZENGE
MOUTHWASH
OIL
OINTMENT
PASTE
PASTE, DENTIFRICE
PATCH, EXTENDED RELEASE
PATCH, EXTENDED RELEASE, ELECTRICALLY CONTROLLED
PELLET
PILL
POWDER
POWDER, DENTIFRICE
POWDER, FOR SOLUTION
POWDER, FOR SUSPENSION
RINSE
SALVE
SHAMPOO
SHAMPOO, SUSPENSION
SOAP
SOLUTION
SOLUTION, CONCENTRATE
SOLUTION, FOR SLUSH
SPONGE
SPRAY
SPRAY, METERED
SPRAY, METERED PUMP
SPRAY, SUSPENSION
STICK
STRIP
SUPPOSITORY
SUPPOSITORY, EXTENDED RELEASE
SUSPENSION
SUSPENSION, EXTENDED RELEASE
SYRUP
TABLET
TABLET, CHEWABLE
TABLET, COATED
TABLET, DELAYED RELEASE
TABLET, DELAYED RELEASE PARTICLES
TABLET, EFFERVESCENT
TABLET, EXTENDED RELEASE
TABLET, FILM COATED
TABLET, FILM COATED, EXTENDED RELEASE
TABLET, MULTILAYER
TABLET, MULTILAYER, EXTENDED RELEASE
TABLET, SOLUBLE
TABLET, SUGAR COATED
WAFER

TABLE II

Generally known Routes of Administration

Topical epicutaneous (application onto the skin)
inhalational
enema
eye drops (onto the conjunctiva)
ear drops
intranasal (into the nose)
vaginal

Enternal by mouth (orally)
by gastric feeding tube
rectally

Parenteral intravenous (into a vein)
intraarterial (into an artery)
intramuscular (into a muscle)
intracardiac (into the heart)
subcutaneous (under the skin)
intraosseous infusion (into the bone marrow)
intradermal, (into the skin itself)
intrathecal (into the spinal canal)
intraperitoneal, (infusion or injection into the peritoneum) is predominantly used in veterinary medicine and animal testing
transdermal (diffusion through the intact skin)
transmucosal (diffusion through a mucous membrane)
inhalational

Other epidural
intravitreal

TABLE III

Generally recognized tempuratures in cold chain compliance

| Category | Temperature Range (stated in C.° and F.°) |
|---|---|
| Frozen | −25° and −10° C. (−13° and 14° F.) |
| Cold | Any temperature not exceeding 8° C. (46° F.) |
| Cool | Between 8° and 15° C. (46° and 59° F.) |
| Temperature Controlled | Thermostat controlled of 20° to 25° C. (68° to 77° F.) |
| Room Temperature | Temperature prevailing in area (no thermostat) |
| Warm | Between 30° and 40° C. (86° to 104° F.) |
| Excessive Heat | Above 40° C. (104° F.) |

TABLE IV

Common Results of variations of temperature outside defined range
Results when drug products recommended to be stored at 15°-25° C. are exposed to temperatures above 30° C.

| Physical Changes | Chemical Changes |
|---|---|
| Separation of emulsion systems | Increased rate of degradation |
| Sedimentation of active ingredients | Increased rate of toxic degradation |
| Loss of "volatile" components and flavoring agents | Increased rate of interaction with direct contact of packaging material |
| Changes in crystalline structure of fatty bases and active ingredients | Increased interactions of components in aqueous solution |

The invention claimed is:

1. A method of fabricating a nanomaterial into a pharmaceutical dosage form, said method comprising,
   a) fabricating a nanomaterial which possesses the functional property of thermal conductivity, to a pharmaceutical dosage form, wherein said dosage form is a pre-filled syringe and wherein said fabricating creates an interface between said nanomaterial and a drug product enclosed within the pre-filled syringe;
   b) interfacing the nanomaterial with a drug product enclosed within the pre-filled syringe, wherein said interfacing creates a boundary between the nanomaterial and said drug product;
   c) enclosing the drug product into the pre-filled syringe, whereby the nanomaterial monitors a drug product property within the pre-filled syringe, and wherein the drug product property is temperature.

2. The method claim 1, wherein the nanomaterial comprises a nanofiller or nanocomposite.

3. The method of claim 2, further comprising a thermal biosensor.

4. The method of claim 2, further comprising a polyhedral oligomeric silsequioxane or colloidal silica.

5. The method of claim 1, wherein the drug product is a vaccine.

* * * * *